(12) United States Patent
Martin

(10) Patent No.: US 9,951,332 B2
(45) Date of Patent: Apr. 24, 2018

(54) SNORNA, COMPOSITIONS AND USES

(71) Applicant: CENTRE NATIONAL DE LA RECHERCHE SCIENTIFIQUE, Paris (FR)

(72) Inventor: Jean-René Martin, Orsay (FR)

(73) Assignee: NINOVAX, Paris (FR)

( * ) Notice: Subject to any disclaimer, the term of this patent is extended or adjusted under 35 U.S.C. 154(b) by 0 days.

(21) Appl. No.: 15/035,327

(22) PCT Filed: Nov. 7, 2014

(86) PCT No.: PCT/EP2014/073991
§ 371 (c)(1),
(2) Date: May 9, 2016

(87) PCT Pub. No.: WO2015/067727
PCT Pub. Date: May 14, 2015

(65) Prior Publication Data
US 2016/0298112 A1    Oct. 13, 2016

(30) Foreign Application Priority Data
Nov. 7, 2013   (FR) ...................................... 13 60889

(51) Int. Cl.
*C12N 15/113*    (2010.01)
*C12Q 1/68*    (2018.01)

(52) U.S. Cl.
CPC .......... *C12N 15/113* (2013.01); *C12Q 1/6876* (2013.01); *C12N 2310/12* (2013.01); *C12N 2320/30* (2013.01); *C12Q 2600/106* (2013.01); *C12Q 2600/136* (2013.01); *C12Q 2600/148* (2013.01); *C12Q 2600/158* (2013.01)

(58) Field of Classification Search
None
See application file for complete search history.

(56) References Cited

PUBLICATIONS

Huang, Z.-P. et al. "Genome-wide analyses of two families of snoRNA genes from *Drosophila melanogaster*, demonstrating the extensive utilization of introns for coding of snoRNAs" *RNA*, Aug. 1, 2005, pp. 1303-1316, vol. 11, No. 8.
Jiang, H. et al. "Intestinal stem cells in the adult *Drosophila* midgut" *Experimental Cell Research*, Jul. 23, 2011, pp. 2780-2788, vol. 317, No. 19.
Kato, M. et al. "Ageing and the small, non-coding RNA world" *Ageing Research Reviews*, Apr. 6, 2012, pp. 429-435, vol. 12, No. 1.
Database EMBL [Online] Accession No. AJ809559, "*Drosophila melanogaster* psi28s-1153 snoRNA gene" Feb. 3, 2005, pp. 1-2, XP-055166324.
Written Opinion in International Application No. PCT/EP2014/073991, dated Feb. 9, 2015, pp. 1-6.

*Primary Examiner* — Tracy Vivlemore
(74) *Attorney, Agent, or Firm* — Saliwanchik, Lloyd & Eisenschenk

(57) ABSTRACT

The present invention concerns the use of particular RNA sequences as a medicament. More precisely, it concerns the use of small nucleolar RNAs (snoRNAs) which the inventor has shown to be involved in the mechanisms of aging. The snoRNAs of the invention can be used in particular to increase the stress resistance of a subject and to fight against the harmful effects of aging, typically for preventing or treating a degenerative disease, a laminopathy, diabetes, obesity or a cancer and, more generally, to prolong the lifespan of a subject. The snoRNAs of the invention can also be used in the treatment of infertility. The invention further relates to vectors, cells, transgenic animals and compositions capable of expressing an snoRNA of the invention, and methods using any of the above products of the invention as a tool for identification of a molecule active in the prevention or treatment of a pathology, abnormality or disorder linked to a mechanism of aging.

12 Claims, 30 Drawing Sheets
(21 of 30 Drawing Sheet(s) Filed in Color)

Control: WC - stomach and intestine wall

Mutant: F4 - stomach and intestine wall

Control: CS-ovaries

Mutant: F4 – ovaries

Targeted expression of snoRNA in enterocytes, under the control of MyoIA-Gal4 (MyoIA-Gal4; UAS-mCD8-GFP)

Targeted expression in enterocytes by MyoIA-Gal4, in the F4 mutant genetic background (MyoIA-Gal4, F4/F4; UAS-8M/+)

Targeted expression in intestinal stem cells (ISc) (esg-Gal4, UAS-GFP)

Targeted expression in enteroblasts: Su(H)-GBE-Gal4; UAS-mCDB-GFP.

Targeted expression in intestinal stem cells (ISc) (Dl-Gal4, UAS-GFP)

Targeted expression under the control of esg-Gal4 (esg-Gal4, F4/F4; UAS-8M/+)

Targeted expression under the control of Su(H)-Gal4 (Su(H)-GBE-Gal4, F4/F4; UAS-8M/+)

Targeted expression under the control of Delta-Gal4 (Delta-Gal4, F4/F4; UAS-8M/+)

```
# STOCKHOLM 1.0

Dmel-psi28S1153    AAAACGUUAG---AUAUUAAACUGUGGUU-GAA-UUCACAAAA
Dsim-psi28S1153    GAAACGUUAG---GUAUAAACCUGUGGUU-GAA-UUCACAAAA
Dsec-psi28S1153    GAAACGUUAG---GUAUUAACCUGUGGUU-UAA-UUCACAAAA
Dyak-psi28S1153    GCAACCGUUGUAUAAUAUUAAACUGUGGAA---ACUUC-ACAAA
Dere-psi28S1153    GCAUGCGUUGAAUAAUAUUAAACUGUGGAC-GAA-UUC-CCAAA
Dana-psi28S1153    UUAGGCGUU-AAAACAUUAAACGUUGGCU--GA-UUU-AUGAU
Dpse-psi28S1153    CAUGGCGCUC-A-AACAUUAAUCGGUGGCC-UGA-UCC-ACACG
Dper-psi28S1153    CAUGGCGCUC-A-AACAUUAAUCGGUGGCC-UGA-UCC-ACACG
Dwil-psi28S1153    AGAGGCGUUC---AACAUUAACUUUAGCCGU-UCUUU-UAAAC
Dmoj-psi28S1153    CCCUGCGUUG---AGCAGUAAAUUGUCGCU-G-A-UUG-AUAAU
Dvir-psi28S1153    UUAUGCGUUC---AACAGUAAAUUGUCGCC-G-A-UAG-AUUAC
Dgri-psi28S1153    UUGUGCGUUC---GACAGUAAAUUUCGAU-G-ACUG---UAGA
                   *** *          *     *   *  *        *
#=GC SS_cons       ...(((((((..........(((.(((((((((.............

UAGGCCAC-AGUUAUGCAA-UAAACGCUAGAAAAA---AAACGGUAGUAUUAAUAACGUG
UAGGCCAC-AGUUAUGCAA-UAAACGCUAGAAAAA---AAACGGUAGUAUUAAUAACGUG
UAGGCCAC-AGUUAUGCAA-UAAACGCUAGAAAAA---AAACGGUAGUAUUAAUAACGUG
UAGGCCAC-AGUUAUGCAA-GAAACGCUAGA-AAA---ACUUGGUAGUAUUAAUAACGUG
UAAGCCAC-AGUUAUGCAA-GAAACGCUAGA-AAA---AAUAGGUAGUAUUAAUAACGUG
UAGGCUAG-UGUUAUGCAC-GCAACGCUAGA-GAA---AAUUGGUAGUAUUAAUAAUGCG
UCGGCCAC-AUUUAUGCAC-GCAGCGCCAGA-U--AAUAGUAGGCAGCAUUAAUAAUGUA
UCGGCCAC-AUUUAUGCAC-GCAGCGCCAGA-U--AAUAGUAGGCAGCAUUAAUAAUGUA
UAAGCUAUUUGUUAUGCAA-GUAACGCUAGA-AUAUAAUUUCUGCAACAUUAAUAAUGCU
UAGGCGAC-GAUAAUGCAA-ACAACGGUAGA----AAAAACUAACGACAUUAAUAAUACA
UAGGCGAC-AGUUAUGCAAGGCAACGCUAGA----AUAAGCAGACGACAUUAAUAAUGCA
UAGGCGAA-AAUUAUGCAAGGCAACGCUAGA-CCAAUUAGAUGACGACAUUAAUAAUGCA
*  ** *   *  *****    *  **   ***               ********
..))))))).)))))......))))))..............(((((((...(((((((

UUGACUAACAUCUGCGGAUAAGA-AGCUUUGCGUUUCAGGUACUAACCACAGUA
UUGACUAACAUCUGCGGAUAAAACAGCUUUGCGUUUCAGGUACUAACCACAGUA
UUGACUAACAUCUGCGGAUAAAUAGCUUUGCGUUUCAGGUACUAACCACAGUA
CUGACUAACGUCUGCGGAUAAA--AGCUUUGCGUUUCAGGUACUAACCACAUUA
CUUACUAACAUCUGCGGAUAAG--AGCUUUGCGUUUCAGGUACUAACCACAAUA
UUGGUGGCAAAUCUAUCGAUUUGAUCUUCGCAUUUCAGGUACUAG-CACAGUU
UUGGUUCCAA-AU--GACUC--AGACUUUUGCAUUUCAGGUUAGCUACAACG
UUGGUUCCAA-AU--GACUC--AGACUUUUGCAUUUCAGGUUAGCUACAAAG
UUGGUCGUAUACU---AACA-AAAAUCUCAGCAUUUGAGGUGCUGCUACAAUU
UUGACCACUAAAU---CCCA--UGAACAUUGCAUUUGAGGUGUC-GCGACAUGU
UUGGCCGACAAAC---UCCA--CGGCCUUUGCGUUUGAGGUGUC-GCCACAUGU
UUGGCCGAUUAAC---UCAG----AU-CUUUGCAUUUGAGGUGUC-GCCACAUGU
**                         ** ********            ***
............................))))))...))))))))..........
```

FIGURE 9A

```
# STOCKHOLM 1.0

Dmel-psi28S1153                    AAAAGCGUUAGAUAUUAAACUGUGGUUGAAUUCACUAAA
hg18-chr11_12822722-12822880       GUAAGUGUA-GCUAGAAAUUGCGGCUGGAUUUCAA-AAU
                                   *** ** *   *** ** ** ** ***    * ***
#=GC SS_cons                       ...(((((((........(((((((((((((...........)
//

AGUGAAAGUAGUCAAUAAACGCUAGAAAAAAAC------GCUAGUAUUUAAUAAC--CUGUUCACUAA
UAGCCAAUUCUGCAAUUUUCACCGCAAUAAAAGCUUCUCCAGUUAUACAUGGUGAUGUGCUUGAUGGG
*** ** ** ****** * *  ** **** *      **  **  *  *   ** ****
)))))))))..........)))))).........(((......(((((((((((.((((((....(((.......

CAUCUGCGGAUA-AGAAGCUU--UGCGUUUUGAGGUACU-AACCACAGUA
CUAUUCUGCACAGACGAGGCUGCUAGGUUGCGGUGGACGGGGCCACAGCU
*  ** *** * **  **   *   ***  *   * **      ******
(((((........)))))......))))))).))))))..))).)))).
```

FIGURE 10 mouse-1 homolog

```
# STOCKHOLM 1.0

Dmel-psi28S1153                 AAAAGCGUUAGAUAUAAACUCUGGUUGAA
mm9-chr15_30336889-30337017     AAAGGGCUUGAAGAAUG----GU--AUGA
                                *** * ***   * *        **   ** *
#=GC SS_cons                    ...((((((.....................
//
```

```
UUCACAAAAUAGGCCACACUUAUGCAAUAAACGCUAGAAAAAAAACGGUAGUAUUUAAUA
UUCAGA--AUG------AACUAUCAGAGAAACUCCAGAGCCAGCA-GGAAACAUU--AUA
****  *   **        *   ***   * **** * ***   *  * **  ***  ***
.............................))))))............((((((((((....
```

```
ACGUGUUGACUAACAUCUGCGGAUAAGAAGCUUUGCGUUUGAGGUACUAACCACAGUA
GAGCCUUUGCUACAAUGUCCUGUUUC-UUUCUUGGCU--UUUAGUUCUGUUCCACAGAU
 *  **  ***  ** * * * *       *** **   ** ** *     ******
((((..........................))))....))))))))))......
```

FIGURE 11A mouse-2 homolog

```
# STOCKHOLM 1.0

Dmel-psi28S1153              AAAAGCGUUAGAUAUUAAACUGUGUUGAAUU
mm9-chr18_6495012-6495133    GAAAGCAUUUAAUAUUUACCAAUAGUUUAU-U
                             ***** **  ****  *  *  * *** *  *

#=GC SS_cons                 ...(((((.....((((((.((((((....
//
```

```
CACAAAAUACGCCACAGUUAUGCAAUAAACGCUAGAAAAAAAACGGUAGUAUUUAAUAA
C-CGAGCUAG----GGUAAAGCAGUCAGUGCUAGAAUAAUG---AGAAAACACAAUA-
* *   ***     **  *** * *   **********          *   *   **** 
...))))))).)....))))))......))))).............................
```

```
GGUGUUGACUAAAAUCUGCGGAUAAGAAGCUUUGCGUUUUGAGGUACUAACCACAGUA
CAUAA-----GACCUCUCAAGGGGAGAUGCU----------GUUACUGUAUAUACUG
* *       ** ***  *   *** ***          * ****    *   * *
............((((....))))........................................
```

FIGURE 11B

Females

Males

1) CG9339: skywalker: 345-400-432-462pb
2) RP49 control 300 bp
3) Non-contamination by genomic DNA control

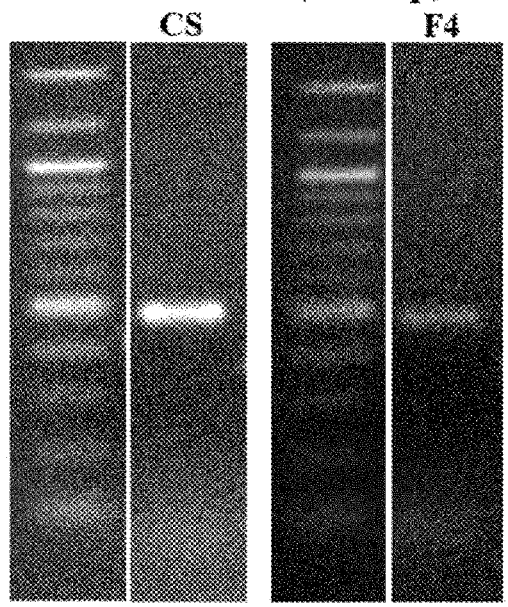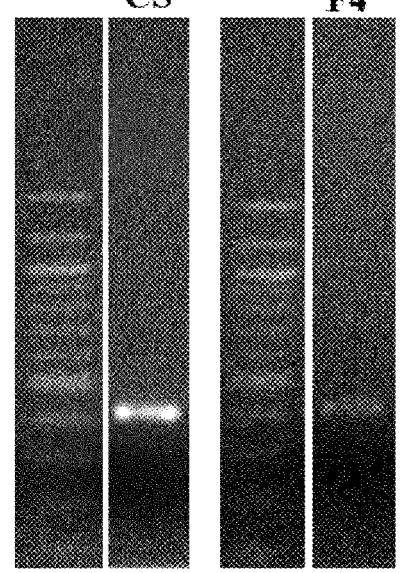
FIGURE 18A  FIGURE 18B

SNORNA, COMPOSITIONS AND USES

CROSS-REFERENCE TO RELATED APPLICATION

This application is the U.S. national stage application of International Patent Application No. PCT/EP2014/073991, filed Nov. 7, 2014.

The Sequence Listing for this application is labeled "Seq-List-replace-2.txt" which was created on Sep. 15, 2017 and is 13 KB. The entire content of the sequence listing is incorporated herein by reference in its entirety.

The present invention concerns the use of particular RNA sequences as a medicament. More precisely, it concerns the use of small nucleolar RNAs (snoRNAs) which the inventor has shown to be involved in the mechanisms of aging. The snoRNAs of the invention can be used in particular to increase the stress resistance of a subject and to fight against the harmful effects of aging, typically for preventing or treating a degenerative disease, in particular neurodegenerative, a laminopathy, in particular Hutchinson-Gilford progeria syndrome (HGPS) (also known as progeria), diabetes, obesity or a cancer and, more generally, to prolong the lifespan of a subject. The snoRNAs of the invention can also be used in the treatment of infertility.

The invention further relates to vectors, cells, transgenic animals and compositions capable of expressing an snoRNA of the invention, and methods using any of the above products of the invention as a tool for identification of a molecule active in the prevention or treatment of a pathology, abnormality, disorder or an apparent or functional deterioration linked to a mechanism of aging.

TECHNOLOGICAL BACKGROUND

The mechanisms of aging (i.e., progressive decline in the capacity to survive and reproduce with age) have perplexed society and the scientific community for centuries. There are two currently prevailing theories, one that aging results from a genetically preprogrammed evolutionary path and the other that aging is a normal consequence of existence during which cellular and molecular damage accumulates. This damage would include oxidative damage induced by free radicals, defective mitochondria, somatic mutations, progressive shortening of telomeres, programmed cell death, proliferation of damaged cells, etc. (Semsei I. (2000) On the nature of aging. Mech Aging Dev 117:93-108).

It has been shown, in organisms like yeast and mice, that caloric reduction exerts a decisive positive impact on lifespan extension (Sohal, R S, Weindruch, R (1998) Oxidative stress, caloric restriction, and aging. Science 273:59-63; Finch, C E, Revkun, G. (2001) The genetics of aging. Annu. Rev. Genom. Hum. Genet. 2:435-462). Recent studies have shown that caloric restriction would also be effective in primates, including humans (Roth, G S, Lasnikov, V, Lesnikov, M, Ingram, D K, Land, M A (2001) Dietary caloric restriction prevents the age-related decline in plasma melatonin levels of rhesus monkeys. J Clin Endocrinol Metab. 86: 3292-5; Roth G S, Lane M A, Ingramn D K, Mattison J A, Elahi D, Tobin J D, Muller D, Metter E J (2002) Biomarkers of caloric restriction may predict longevity in humans. Science. 297: 811-813; Walford R L, Mock D, Verdery R, MacCallum T. (2002) Calorie restriction in biosphere 2: alterations in physiologic, hematologic, hormonal, and biochemical parameters in humane restricted for a 2-year period. J Gerontol A Biol Sci Med Sci 57: 211-24). Unfortunately, it is probable that the majority of humans are not capable of following the strict diet required to benefit from this discovery.

For several years, many research groups have been dedicated to identifying the genes and signalling pathways involved in the aging process. The studies reported here are conducted in numerous organisms, including yeast *Saccharomyces cerevisiae*, worm *Caenorhabditis elegans* and fly *Drosophila melanogaster* (Fontana et al., 2010), and permitted identifying a growing list of genes. Many of them are involved in hormone signalling and are conserved in a large variety of eukaryotic organisms. It has become clear that, at least for lower species, the pathways responsible for development and growth at the start of life retain a lifelong influence and even partially condition its duration. These studies have also indirectly shown the importance of metabolic capacity and stress resistance for evaluating the lifespan of a subject.

For example, mutants of the clk-1 gene of *Caenorhabditis elegans* were involved in reducing the extra-mitochondrial production of reactive oxygen species (Hekimi, S, Guarente, L. (2003) Genetics and the specificity of the aging process. Science 299:1351-1354). WO 98/17823 describes the function of the clk-1 gene in the processes of development and longevity. It particularly claims a method to increase an individual's lifespan by regulation of clk-1 gene expression.

A mutation of the Methuselah gene (which codes for a G-protein coupled receptor) has also been described as capable of increasing the lifespan of *Drosophila* by around 35% (U.S. Pat. No. 6,303,768).

Telomere shortening is also known as a mechanism responsible for cell aging. In vertebrates, telomerase is a ribonucleoprotein (RNP) reverse transcriptase whose role is to maintain the length of telomeres by addition of telomeric DNA to the end of chromosomes in dividing eukaryotic cells (Kiss, 2002). In humans, a mutation in the H/ACA box of telomerase snoRNA causes a pleiotropic genetic disease, dyskeratosis congenita, whose patients present shorter telomeres (Mitchell et al., 1999; Vulliamy et al., 2001). Despite the efforts of the scientific community to decode the mechanisms of aging and identify new therapeutic targets to delay this process and/or combat its harmful effects, the tools available remain insufficient. The need for tools that permit "aging well", that is without the diseases and discomforts generally associated with old age, is felt all the more now that medical progress combined with general improvement in life conditions have already permitted the human population, in just a few decades, to increase its life expectancy in a very significant manner.

SUMMARY OF THE INVENTION

The present invention relates to the prophylactic or therapeutic use of the RNA sequences of interest for which the inventor has demonstrated particular involvement in the mechanisms of aging. They have especially shown the ability of these sequences to spectacularly increase the lifespan of a subject by stopping the mechanisms of aging and fighting the harmful effects associated therewith. The sequences of the invention also fight diseases associated with aging, such as degenerative diseases, laminopathies and cancers, as well as diabetes and obesity. They have proven especially effective in the treatment of infertility or sterility (i.e., difficulty conceiving or inability to conceive) as well as increasing the resistance of subjects, in particular subjects who have reached sexual maturity, preferably elderly subjects, to stress.

A first subject of the invention relates to an isolated or synthetic RNA sequence comprising SEQ ID NO: 1, a homologous sequence, preferably an orthologous sequence, or a functionally analogous sequence, for use as a medicament.

The inventor has demonstrated that the RNA sequence SEQ ID NO: 1 discovered in *Drosophila* corresponds to orthologous sequences in mammals such as primates and human beings, and in rodents such as mice and rats. The invention also covers the use, in one or the other of the applications described in this text, of an isolated or synthetic RNA sequence preferably chosen from SEQ ID NO: 2 of human origin and SEQ ID NOs: 3 and 4 of mouse origin. SEQ ID NOs: 2, 3, 4, 9, 11, 13, 15, 17, 19, 21, 22, 24, 26, and 28 identified in Table 1 of this text are examples of sequences orthologous to SEQ ID NO: 1.

Another subject of the invention is a DNA sequence coding for an RNA sequence of interest according to the invention.

The invention also concerns a vector permitting in vitro, ex vivo or in vivo expression of an RNA sequence according to the invention.

The invention also concerns a cell comprising an RNA sequence according to the invention or transformed by a vector according to the invention, as well as a composition comprising a product according to the invention and a dietarily- or pharmaceutically-acceptable support.

The invention also concerns the use of an RNA sequence, vector, cell or a composition according to the invention, continuously or sequentially, to restore or modulate the expression of said RNA sequence in vivo, in vitro or ex vivo.

Another object of the invention is a transgenic mouse whose genome has been genetically modified to prevent or modify, preferably alter, the expression of an RNA sequence of interest according to the invention, typically one and/or the other of SEQ ID NOs: 3 and 4.

The invention also covers a method for evaluating the cosmetic or therapeutic efficacy of a test compound to fight the harmful effects of aging or stress, or to fight infertility, said method comprising i) exposure of a cell or population of cells not expressing the RNA sequence of the invention or expressing an abnormal version of said RNA sequence, or a transgenic mouse according to the invention, ii) evaluation of the effects, if any, of the test compound on the phenotype of said cell(s) or said transgenic mouse, and iii) determination of the cosmetic or therapeutic efficacy of said test compound, a restoration of the activity and/or expression of said RNA sequence being correlated with efficacy of said test compound.

The invention also covers a method for evaluating the cosmetic or therapeutic efficacy of a test compound to fight the harmful effects of aging or stress, or to fight infertility, said method comprising i) exposure of a cell according to the invention comprising an RNA sequence according to the invention or a population of cells comprising a cell according to the invention, ii) evaluation of the effects, if any, of the test compound on the phenotype of said cell or population of cells, and iii) determination of the cosmetic or therapeutic efficacy of said test compound, an increase of the activity and/or expression of said RNA sequence being correlated with efficacy of said test compound.

The invention also concerns kits comprising nucleic acids, vectors, cassettes and/or cells such as described previously.

DETAILED DESCRIPTION

The invention results from the demonstration by the inventor of the influence of a small sequence of nucleolar DNA (snoRNA:Ψ28S-1153 called "youth", identified in this text as SEQ ID NO: 1) on the lifespan of *Drosophila*. This snoRNA has been identified as part of a systematic screening of snoRNAs associated with the *Drosophila* genome (Huang et al., 2005) without any function being ascribed to it to date.

The inventor has characterized this sequence and notably shown that a genomic deletion of 632 base pairs of the F4 region of the *Drosophila* genome containing the snoRNA: Ψ28S-1153 shortens the lifespan of *Drosophila* by around 30%. They then demonstrated that the overexpression of this RNA sequence, for example using a transgene containing genomic DNA coding for this snoRNA, spectacularly increases the lifespan of *Drosophila* by around 100%. Flies overexpressing the RNA sequence of the invention live up to twice as long. Furthermore, the inventor has identified and detected the expression of orthologous "youth" sequences in mice and humans.

Characteristics of the RNA Sequences and Other Products of the Invention

As explained previously, the invention concerns an isolated or synthetic ribonucleotide sequence (RNA sequence) with the functional characteristics of SEQ ID NO: 1 identified originally in *Drosophila* (*Drosophila melanogaster*) for use as a medicament in a subject who can benefit from it, typically an animal or insect, for example a mammal or a rodent, preferably a human being.

"Medicament" means a substance possessing preventive or curative properties. In the context of the invention, a medicament is intended to cure, promote cure, relieve or prevent, in a subject as defined previously, a pathology, abnormality or impairment related to an abnormal or simply undesirable aging process.

In *Drosophila*, the RNA sequence of interest is comprised in the genomic region identified as region F4, itself located on chromosome 2R. This nucleotide sequence is, for the first species of *Drosophila* (*Drosophila melanogaster*) studied by the inventor, constituted of 148 base pairs. It is identified in this text as SEQ ID NO: 1.

Homologs/orthologs as well as functional analogs and variants of SEQ ID NO: 1 are, likewise, sequences of interest that are objects of the present invention.

The term "homolog" is used in the context of the present invention to designate a structure whose nucleotide sequence is identical or sufficiently close to that of SEQ ID NO: 1, identified in this first species of *Drosophila*, to be considered as its equivalent in another species (*Drosophila*, insect, or any other animal). A sequence is considered as a homolog of SEQ ID NO: 1 if it has therewith, or with a fragment thereof of at least 50 consecutive nucleotides, a sequence identity of at least 70%, 80% or 85%, preferably at least 90 or 95%, more preferably at least 96, 97, 98 or 99% obtained, for example, by the blastN sequence alignment program (Altschul et al., 1990), or by the INFERNAL program for "INFErence of RNA ALignment", which identifies DNA sequences from RNA structure and their sequence similarity. Two homologous genetic sequences of two different species are considered orthologs if they descend from a unique sequence present in the last common ancestor of the two species.

The percentage of identify is determined by comparing two sequences for which an optimal alignment has been done. The percentage of identity is calculated by determining the number of positions for which an identical residue appears over both sequences at the same position divided by the total number of positions and multiplied by 100. The optimal alignment of the two sequences can be obtained, for example, with a local homology search algorithm (Smith and Waterman, 1981) or equivalent systems known to the person skilled in the art.

The term "analog" designates any mimetic that is a chemical compound existing in nature and isolated therefrom, or produced artificially, and which has at least one of the endogenous functions of the nucleotide sequence that it imitates (functionally-equivalent RNA sequence), for example all the endogenous functions of the nucleotide sequence which it imitates. An example of an analog compound consists, for example, in a sequence permitting splicing the same genes. A particular object of the invention therefore concerns a sequence analogous to SEQ ID NO: 1 that permits splicing one or more genes chosen from among Ir56d, buttonhead, klarsicht, CG3262, CG30502 (fatty acid 2-hydroylase—fa2h), CG11125, CG9339, and CG40006 of *Drosophila melanogaster*. Experiments conducted by the inventor have demonstrated, for example, that gene CG9339 (called skywalker) (Uytterhoeven et al., 2011) is not correctly spliced in the F4 mutant, indicating that the youth snoRNA is involved in the alternative splicing of this gene (see FIG. 17). Similar results have also been obtained for a transcript of the klarsicht gene, for which less spliced RNA is observed in the F4 mutant than in the Canton-S wildtype control flies (FIG. 18A), as well as for gene CG30502, coding for gene fa2h (FIG. 18B), the latter having been involved in humans in various forms of demyelination, such as neurodegeneration related to the accumulation of iron, leukodystrophies (typically those related to fa2h gene mutations) and hereditary spastic paraplegia (typically SPG35 hereditary spastic paraplegia) (Dick et al., 2008; 2010; Pierson et al., 2012).

The term "functional variant" means any nucleic acid having one or more modifications or mutations (for example, a deletion, substitution or addition of one or more bases) relative to parent sequences described in this application, and permitting the applications described in the context of the present invention.

A sequence considered to be a homolog, preferably an ortholog, of a reference sequence in the sense of the invention is an example of a functional variant in the sense of the invention of said reference sequence. Such a sequence can be natural, recombinant or synthetic.

SEQ ID NO: 1 is a highly conserved sequence throughout evolution and present in many animal species. The inventor has therefore notably shown that this sequence is present in the 12 other species of *Drosophila* whose genome is known. Examples of sequences homologous/orthologous to RNA SEQ ID NO: 1 therefore also comprise RNA SEQ ID NOs: 9, 11, 13, 15, 17, 19, 21, 22, 24, 26, and 28 identified in Table 1 of this text (see FIG. 9).

The inventor has also identified an orthologous RNA sequence in the human being, located on chromosome 11, in positions 12822722-12822811. It is the sequence identified in this text as SEQ ID NO: 2. The inventor has also identified two orthologous RNA sequences in mice (these are the sequences identified, respectively, as SEQ ID NOs: 3 and 4 in this text), located on chromosome 15, in positions 30336889-30337017 (SEQ ID NO: 7) and on chromosome 18, in positions 6495012-6495091 (SEQ ID NO: 8).

Nucleotide sequences of interest identified in *Drosophila*, humans and mice are listed in Table 1 below.

TABLE 1

| Species | RNA sequences (from 5' to 3') | SEQ ID NO: |
|---|---|---|
| *Drosophila melanogaster* | AAAGCGUUAGAUAUUAAACUGUGGUUGAAUUCACAAA AUAGGCCACAGUUAUGCAAUAAACGCUAGAAAAAAAAC GGUAGUAUUUAAUAACGUGUUGACUAACAUCUGCGGAU AAGAAGCUUUGCGUUUUGAGGUACUAACCACAGUA | 1 |
| Human | GUAAGUGUAGCCUAGAAAUUGGGGCUGGAUUUGAAAA UUAGCCCCAAUUCUGCAAUUUUCACCGCAAUAAAAGCU UCUCCAGUUAUACAUGGUGAUUGGUCUUGAUGGGCUAU UGUGGACAGAGGAGGGUGCUAGGUUGGGGUGGACGGG GCCACAGCU | 2 |
| Mouse-1 | AAAGGGGUUGAAGAAUGGUAUGGAUUCAGAAUGAACU AUCAGAGAAACUCCAGAGCCAGCAGGAAACAUUAUAGA GCCUUUGCUACAAUGUCCUGUUUCUUUCUUGGCUUUUA GUUCUGUUCCACAGAU | 3 |
| Mouse-2 | GAAAGCAUUUAAUAUUUACCAAUAGUUUAUUCCGAGCU AGGGUAAAGCAGUCAGUGCUAGAAAAAUGAGAAAACAC AAUACAUAAGACCUCUCAAGGGGAGAUGCUGUUACUGU AUAUACUG | 4 |
| *Drosophila simulans* | AAAGCGUUAGGUAUAAACCUGUGGUUGAAUUCACAAA UAGGCCACAGUUAUGCAAUAAACGCUAGAAAAAAACG GUAGUAUUUAAUAACGUGUUGACUAACAUCUGCGGAUA AAACAGCUUUGCGUUUUGAGGUACUAACCACAGUA | 9 |
| *Drosophila sechellia* | AAAGCGUUAGGUAUUAACCUGUGGUUUAAUUCACAAA UAGGCCACAGUUAUGCAAUAAACGCUAGAAAAAAAACG GUAGUAUUUAAUAACGUGUUGACUAACAUCUGCGGAUA AAAUAGCUUUGCGUUUUGAGGUACUAACCACAGUA | 11 |
| *Drosophila yakuba* | CAAGCGUUGUAUAAUAUUAAACUGUGGAAACUUCACAA AUAGGCCACAGUUAUGCAAGAAACGCUAGAAAAACUUG GUAGUAUUUAAUAACGUGCUGACUAACGUCUGCGGAUA AAAGCUUUGCGUUUUGAGGUACUAACCACAUUA | 13 |
| *Drosophila erecta* | CAUGCGUUGAAUAAUAUUAAACUGUGGACGAAUUCCCA AAUAAGCCACAGUUAUGCAAGAAACGCUAGAAAAAAUA GGUAGUAUUUAAUAACGUGCUGACUAACAUCUGCGGAU AAGAGCUUUGCGUUUUGAGGUACUAACCACAAUA | 15 |

TABLE 1-continued

| Species | | SEQ ID NO: |
|---|---|---|
| Drosophila ananassae | UUAGGCGUUCAAAACAUUAAACGUUGGCUGAUUUAUGA UUAGGCUAGUGUUAUGCACGCAACGCUAGAGAAAAUUG GUAGUAUUUAAUAAUGCGUUGGUGGCAAAUCUAUCGA UUUUGAUCUUCGCAUUUUGAGGUACUAGCACAGUU | 17 |
| Drosophila pseudoobscura | CAUGGCGCUCAAACAUUAAUCGGUGGCCUGAUCCACAC GUCGGCCACAUUUAUGCACGCAGCGCCAGAUAAUAGUA GGCAGCAUUUAAUAAUGUAUUGGUUCCAAAUGACUCAG ACUUUUGCAUUUUGAGGUGUUAGCCACAACG | 19 |
| Drosophila persimilis | CAUGGCGCUCAAACAUUAAUCGGUGGCCUGAUCCACAC GUCGGCCACAUUUAUGCACGCAGCGCCAGAUAAUAGUA GGCAGCAUUUAAUAAUGUAUUGGUUCCAAAUGACUCAG ACUUUUGCAUUUUGAGGUGUUAGCCACAAAG | 21 |
| Drosophila willistoni | AGAGGCGUUCAACAUUUAACUUUAGCCGUUCUUUUAAA CUAAGCUAUUUGUUAUGCAAGUAACGCUAGAAUAUAAU UUCUGCAACAUUUAAUAAUGCUUUGGUCGUAUACUAAC AAAAAUCUCAGCAUUUUGAGGUGUCUGCUACAAUU | 22 |
| Drosophila mojavensis | CCCUGCGUUGAGCAGUAAAUUGUCGCUGAUUGAUAAUU AGGCGACGAUAAUGCAAACAACGGUAGAAAAAACUAAC GACAUUUAAUAAUACAUUGACCACUAAAUCCCAUGAAC AUUGCAUUUUGAGGUGUCGCGACAUGU | 24 |
| Drosophila virilis | UUAUGCGUUCAACAGUAAAUUGUCGCCGAUAGAUUACU AGGCGACAGUUAUGCAAGGCAACGCUAGAAUAAGCAGA CGACAUUUAAUAAUGCAUUGGCCGACAAACUCCACGGC CUUUGCGUUUUGAGGUGUCGCCACAUGU | 26 |
| Drosophila grimshawi | UUGUGCGUUCGACAGUAAAUUUCGAUGACUGUAGAUA GGCGAAAAUUAUGCAAGGCAACGCUAGACCAAUUAGAU GACGACAUUUAAUAAUGCAUUGGCCGAUUAACUCAGAU CUUGCAUUUUGAGGUGUCGCCACAUGU | 28 |

| Corresponding DNA sequences | | |
|---|---|---|
| Drosophila melanogaster | AAAGCGTTAGATATTAAACTGTGGTTGAATTCACAAAAT AGGCCACAGTTATGCAATAAACGCTAGAAAAAAACGGTA GTATTTAATAACGTGTTGACTAACATCTGCGGATAAGAA GCTTTGCGTTTTGAGGTACTAACCACAGTA | 5 |
| human | GTAAGTGTAGCCTAGAAATTGGGGCTGGATTTGAAAATT AGCCCCAATTCTGCAATTTTCACCGCAATAAAAGCTTCTC CAGTTATACATGGTGATTGGTCTTGATGGGCTATTGTGGA CAGAGGAGGGTGCTAGGTTGGGGTGGACGGGGCCACAG CT | 6 |
| mouse-1 | AAAGGGGTTGAAGAATGGTATGGATTCAGAATGAACTAT CAGAGAAACTCCAGAGCCAGCAGGAAACATTATAGAGCC TTTGCTACAATGTCCTGTTTCTTTCTTGGCTTTTAGTTCTG TTCCACAGAT | 7 |
| Mouse-2 | GAAAGCATTTAATATTTACCAATAGTTTATTCCGAGCTAG GGTAAAGCAGTCAGTGCTAGAAAAATGAGAAAACACAA TACATAAGACCTCTCAAGGGGAGATGCTGTTACTGTATAT ACTG | 8 |
| Drosophila simulans | AAAGCGTTAGGTATAAACCTGTGGTTGAATTCACAAAAT AGGCCACAGTTATGCAATAAACGCTAGAAAAAAAACGGT AGTATTTAATAACGTGTTGACTAACATCTGCGGATAAAA CAGCTTTGCGTTTTGAGGTACTAACCACAGTA | 10 |
| Drosophila sechellia | AAAGCGTTAGGTATTAACCTGTGGTTTAATTCACAAAATA GGCCACAGTTATGCAATAAACGCTAGAAAAAAACGGTA GTATTTAATAACGTGTTGACTAACATCTGCGGATAAAATA GCTTTGCGTTTTGAGGTACTAACCACAGTA | 12 |
| Drosophila yakuba | CAAGCGTTGTATAATATTTAAACTGTGGAAACTTCACAAA TAGGCCACAGTTATGCAAGAAACGCTAGAAAAAACTTGGT AGTATTTAATAACGTGCTGACTAACGTCTGCGGATAAAA GCTTTGCGTTTTGAGGTACTAACCACATTA | 14 |
| Drosophila erecta | CATGCGTTGAATAATATTTAAACTGTGGACGAATTCCCAA ATAAGCCACAGTTATGCAAGAAACGCTAGAAAAAAATAGG TAGTATTTAATAACGTGCTGACTAACATCTGCGGATAAG AGCTTTGCGTTTTGAGGTACTAACCACAATA | 16 |
| Drosophila ananassae | TTAGGCGTTCAAAACATTAAACGTTGGCTGATTTATGATT AGGCTAGTGTTATGCACGCAACGCTAGAGAAAATTGGTA GTATTTAATAATGCGTTGGTGGCAAATCTATCGATTTTGA TCTTCGCATTTTGAGGTACTAGCACAGTT | 18 |
| Drosophila pseudoobscura | CATGGCGCTCAAACATTAATCGGTGGCCTGATCCACACG TCGGCCACATTTATGCACGCAGCGCCAGATAATAGTAGG CAGCATTTAATAATGTATTGGTTCCAAATGACTCAGACTT TTGCATTTTGAGGTGTTAGCCACAACG | 20 |
| Drosophila persimilis | CATGGCGCTCAAACATTAATCGGTGGCCTGATCCACACG TCGGCCACATTTATGCACGCAGCGCCAGATAATAGTAGG CAGCATTTAATAATGTATTGGTTCCAAATGACTCAGACTT TTGCATTTTGAGGTGTTAGCCACAAAG | 22 |

TABLE 1-continued

| Species | | SEQ ID NO: |
|---|---|---|
| Drosophila willistoni | AGAGGCGTTCAACATTTAACTTTAGCCGTTCTTTTAAACT AAGCTATTTGTTATGCAAGTAACGCTAGAATATAATTTCT GCAACATTTAATAATGCTTTGGTCGTATACTAACAAAAAT CTCAGCATTTTGAGGTGTCTGCTACAATT | 24 |
| Drosophila mojavensis | CCCTGCGTTGAGCAGTAAATTGTCGCTGATTGATAATTAG GCGACGATAATGCAAACAACGGTAGAAAAAACTAACGA CATTTAATAATACATTGACCACTAAATCCCATGAACATTG CATTTTGAGGTGTCGCGACATGT | 26 |
| Drosophila virilis | TTATGCGTTCAACAGTAAATTGTCGCCGATAGATTACTAG GCGACAGTTATGCAAGGCAACGCTAGAATAAGCAGACGA CATTTAATAATGCATTGGCCGACAAACTCCACGGCCTTTG CGTTTTGAGGTGTCGCCACATGT | 28 |
| Drosophila grimshawi | TTGTGCGTTCGACAGTAAATTTTCGATGACTGTAGATAGG CGAAAATTATGCAAGGCAACGCTAGACCAATTAGATGAC GACATTTAATAATGCATTGGCCGATTAACTCAGATCTTGC ATTTTGAGGTGTCGCCACATGT | 30 |

One particular subject of the invention concerns the use of RNA SEQ ID NO: 1 to identify a target gene, characterized in that said SEQ ID NO: 1 is capable of recognizing a target sequence within a *Drosophila melanogaster* gene preferably chosen from among Ir56d, buttonhead, klarsicht, CG3262, CG30502 (fatty acid 2-hydroylase: fa2h), CG11125, CG9339, and CG40006, said target sequence being preferably chosen from among SEQ ID NO: 31 (TGGTTGAAT-TCACAAAA), SEQ ID NO: 32 (TTGAATTCA-CAAAATA), SEQ ID NO: 33 (AATTCACAAAATAGGC), SEQ ID NO: 34 (AAGCGTTAGATATTAA), SEQ ID NO: 35 (ACATCTGCGGATAAGA), SEQ ID NO: 36 (AAGCTTTGCGTTTTGA), and SEQ ID NO: 37 (AGAAGCTTTGCGTTTT), or an analogous sequence thereof.

In the context of the present invention, the RNA sequences of interest are preferably in the form of snoRNAs. In the context of the invention, the term "snoRNAs" encompasses a group of non-coding RNAs present in all eukaryotic cells. They are located in the nucleus and more particularly in the nucleolus where they are associated with proteins with which they form small nucleolar ribonucleoproteins or snoRNPs. They are generally produced from pre-mRNA introns.

On the evolutionary scale, these non-coding RNAs are present from archaea to mammals. snoRNAs can have several functions, such as modification of ribosomal RNA, like 2'-O-ribose methylation or pseudouridylation of various classes of RNA. They have been involved in the nucleolytic process of ribosomal RNAs and even in the synthesis of telomeric DNA (Kiss, 2002; Kiss et al., 2010; Ye, 2007). There are two main classes of snoRNAs: one comprising a C/D box and one comprising an H/ACA box (FIG. 2A). C/D boxes serve as a guide for 2'-O-ribose methylation on specific sites, while H/ACA boxes direct the conversion of uridine into pseudouridine (Kiss, 2002; Gardner et al., 2010; Huang et al., 2005) (FIG. 2B).

The snoRNA:Ψ28S-1153 (youth) of interest, identified in a first species of *Drosophila*, belongs to the H/ACA class, that is, its structure comprises an H/ACA box. It would therefore be involved in pseudouridylation (i.e., the conversion of uridine into pseudouridine) during the maturation of ribosomal RNA, and would regulate the protein synthesis of certain genes.

The snoRNAs according to the invention can be chemically modified, typically to increase the resistance of the snoRNAs to nucleases, to confer a better affinity/selectivity and therefore a better functionality of the snoRNAs. The modifications typically concern a nucleoside or internucleoside link. They can concern the sugar, for example (typically the 2' position of the sugar), the nitrogenous base of the nucleoside (which typically comprises a substituent in position 2, 4 or 6) or one (or more) phosphate groups.

The modification may consist, for example, of an amination, halogenation, for example fluoridation, or alkylation, for example methylation. A modified sugar group can therefore be chosen, for example, from among the 2'-O-methyl and 2'-O-methoxyethyl groups.

A modified nucleotide can be a nucleotide comprising a heterocyclic base incapable of creating hydrogen bonds with heterocyclic DNA or RNA bases.

The modification of the internucleoside link is, for example, chosen from among a phosphorothioate, methylphosphonate, phosphotriester, phosphorodithioate and phosphoselenate bond.

The present invention also concerns the deoxyribonucleotide sequences (DNA) responsible for the expression of the RNA sequences of interest of the invention. The DNA sequence permitting the expression of RNA SEQ ID NO: 1 is the sequence identified in the present invention as SEQ ID NO: 5, the one permitting the expression of SEQ ID NO: 2 is the sequence identified in the present invention as SEQ ID NO: 6, the one permitting the expression of SEQ ID NO: 3 is the sequence identified in the present invention as SEQ ID NO: 7, and the one permitting the expression of SEQ ID NO: 4 is the sequence identified in the present invention as SEQ ID NO: 8.

One object of the invention therefore also concerns an isolated or synthetic DNA sequence selected from the group comprising SEQ ID NO: 5, SEQ ID NO: 6, SEQ ID NO: 7, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, and characterized in that it permits the expression of an RNA sequence of interest according to the invention.

Like the snoRNAs, the DNAs according to the invention can be modified chemically (see the chemical modifications possible above).

The invention also concerns any recombinant expression cassette, characterized in that it comprises a nucleic acid sequence of interest according to the invention such as defined in this text. The term expression cassette designates a nucleic acid construct/construction comprising a nucleic acid sequence permitting the expression of an RNA sequence of interest according to the invention and a regulator region, operably linked. The expression "operably linked" indicates that the components are combined so that the expression of the nucleic acid sequence (responsible for the expression of the RNA sequence of interest) and/or the targeting of the RNA sequence of interest are under control of the transcriptional promoter. Typically, the promotor sequence is placed upstream of the nucleic acid sequence, at a distance from the latter compatible with expression control. Spacer sequences can be present, between the regulator elements and the coding sequence, as long as they do not impede the expression and/or targeting of the RNA sequence of interest.

Another object of the invention concerns any (expression) vector comprising a nucleic acid or a cassette such as previously defined permitting the expression of an RNA sequence of interest according to the invention in a host cell or a host organism. The vector can be a DNA or RNA, circular or otherwise, single or double strand. It is typically a plasmid, phage, viral vector (chosen, for example, from among an adenoviral vector, a retroviral vector, an adenovirus-associated vector, a lentiviral vector, a poxvirus vector, a herpetic vector, etc.), a cosmid or an artificial chromosome. Advantageously, it is a vector capable of transforming a eukaryotic cell, preferably an animal cell, typically a human cell, preferably a cell of intestinal or ovarian origin. Such vectors are well known to the person skilled in the art and are particularly described in WO 06/085016 and in Barton and Medzhitov, 2002; Tiscornia et al., 2004; Xia et al., 2002; and Shen et al., 2003.

One preferred vector permitting the expression of an RNA sequence of interest according to the invention can be chosen from among, for example, a plasmid, a cosmid, a viral vector or a phage. One preferred vector usable in particular in *Drosophila* is the pChs-Gal4 vector, in which is inserted, upstream of the Gal4 transcription factor, a specific DNA sequence known to regulate the expression of a given gene in a given tissue, such as Myo1A-Gal4, snail-Gal4, Su (H)-GBE-Gal4, or Delta-Gal4. Simultaneously, a second vector (pUAs-snoRNA) comprising the effector gene of interest, here the snoRNA, is preferably positioned downstream of the UAS (Upstream Activating Sequence) regulatory sequences, these latter being recognized by the P[GAL4] transcription factor. Each of these two vectors is then introduced by transgenesis into an animal. These two animal lines are then crossed. This system is called P[GAL4] binary expression system (Brand and Perrimon, 1993; Elliott and Brand, 2008). Therefore, more specifically, the Myo1A-Gal4, snail-Gal4, Su(H)-GBE-Gal4 and Delta-Gal4 vectors comprise a promotor and regulator elements promoting the expression of said RNA sequence in intestinal cells, while the nanos-Gal4 or MTD-(maternal-Tubulin)-Gal4 vectors comprise a promotor and regulator elements promoting expression of said RNA sequence in the ovaries.

The vectors of the invention can also comprise an origin of replication, a selection gene, a reporter gene and/or a recombination sequence. The vectors can be constructed by standard molecular biology techniques, well known to the person skilled in the art, using, for example, restriction, ligation, cloning, replication, etc. enzymes. Specific examples of vectors in the sense of the invention are provided in the experimental part. These vectors may include, for example, the P[GAL4] binary system mentioned above (Brand and Perrimon, 1993; Elliott and Brand, 2008).

The invention also concerns a cell comprising an RNA sequence according to the invention or transformed by means of a construct or vector according to the invention. The cell is preferably an intestinal or ovarian cell. Even more preferred, it is an intestinal stem cell, an enteroblast, an enterocyte, an entero-endocrine cell, a nurse cell or an oocyte.

The invention also comprises the use of a product according to the invention, typically an RNA sequence, a DNA sequence, a vector or a cell according to the invention, continuously or sequentially, to restore or modulate, typically amplify, in vitro, ex vivo or in vivo, the expression of the RNA sequence of interest according to the invention.

The invention also concerns a transgenic mouse whose genome (typically SEQ ID NO: 7 or SEQ ID NO: 8) has been genetically modified, using techniques well known to the skilled person, to prevent or modify, for example increase or decrease, expression, preferably to alter expression, of one or the other of SEQ ID NO: 3 and SEQ ID NO: 4.

The mouse is advantageously genetically modified by homologous recombination (knock-in, knock-out, knockdown) techniques known to the skilled person, including, for example, the use of the CRE/LOX system.

The invention also concerns compositions comprising an RNA sequence, a DNA sequence, a construct, a vector or a cell according to the invention.

The RNA sequences of the invention are very stable and very resistant in vitro. However, in the case of an administration to a subject to be treated, the compositions according to the invention may also advantageously comprise a dietarily- or pharmaceutically-acceptable support.

The expression "dietarily-acceptable support" designates a carrier permitting the subject to ingest and digest without risk the composition comprising an RNA sequence, a construct, a vector or a cell according to the invention comprising such a sequence, and capable of protecting said sequence from any attack, in particular related to food digestion, that could alter it before it produces its therapeutic action.

The expression "pharmaceutically-acceptable support" designates a carrier permitting risk-free administration of the composition comprising an RNA sequence, a construct, a vector or a cell according to the invention comprising such a sequence, according to one of the possible administration routes described below.

Advantageously, the carrier of the present composition facilitates penetration of the RNA of interest, the construct or the expression vector according to the invention into cells, ideally into particular cells as identified in this text, of the subject being treated, and/or protects the RNA, the construct or the expression vector from any damage that may impair its efficacy.

The choice of carrier as well as the content of active substance in the carrier are generally determined relative to the solubility and chemical properties of the active substance, the mode of administration and the characteristics of the subject to be treated.

Usable carriers or supports, acceptable pharmaceutically, include natural cationic polymers such as chitosan or atelocollagen, or synthetic polymers, such as poly(L-lysine), polyethyleneimine (PEI) or dendrimers, which form complexes with the nucleic acids of the invention; liposomes; cationic liposomes; galactosylated liposomes; liposomes coated with a ligand allowing them to target a cell type, such as immunoliposomes coated with an antibody specific for the target cell (Zheng et al., 2009); liposomes positioned within a nanoparticle formed by polymers (Carmona et al., 2009); or even multilayer films of polycations and polyanions.

Excipients such as lactose, sodium citrate, calcium carbonate, and dicalcium phosphate and disintegrating agents such as starch, alginic acids and certain complex silicates combined with lubricants such as magnesium stearate, sodium lauryl sulfate and talc can be used to prepare tablets. To prepare a lozenge, it is advantageous to use lactose and high molecular weight polyethylene glycols. Aqueous suspensions contain emulsifiers or agents that facilitate suspension. Diluents such as sucrose, ethanol, polyethylene glycol, propylene glycol, glycerol and chloroform or mixtures of these are also usable.

Adjuvants such as aluminum salts (for example, aluminum hydroxide, aluminum phosphate, and aluminum sulfate), surfactants (such as lysolecithin, pluronic polyols, polyanions, peptides and emulsions), complete and incomplete Freund's adjuvant, MPL-TDM adjuvant (monophosphoryl lipid A, synthetic trehalose dicorynomycolate), tyrosine, aluminum, saponins such as Stimulon™, and cytokines can also be added to improve the efficiency of the composition. The RNA sequences of the invention can be prepared with an agent, such as injectable microspheres, bioerodible particles, polymeric compounds (such as polylactic acid or polyglycolic acid), beads or liposomes that may provide controlled or sustained release of the product.
Examples of Dietarily-Acceptable Supports Comprise, for Example, Sugars, Saponins, Etc.

The composition may also include one or more other active ingredients chosen preferably among an agent usable in the treatment of a laminopathy, in particular in treating Hutchinson-Gilford progeria syndrome or HGPS (also known as progeria, which consists of early and accelerated aging in humans), obesity, diabetes, cancer, degenerative diseases, in particular neurodegenerative (e.g., leukodystrophy or hereditary spastic paraplegia, also identified as SPG35), stress or infertility.

An active principle in the treatment of obesity may be, for example, leptin or one of its derivatives.

An active principle in the treatment of diabetes may be, for example, insulin or one of its derivatives.

An active principle in the treatment of cancer may be, for example, a conventional cytotoxic chemotherapeutic agent selected from an inhibitor of DNA replication (such as DNA binding agents, in particular intercalating or alkylating compounds), an anti-metabolite agent (such as DNA polymerase inhibitors or a topoisomerase I or II inhibitor), an anti-mitogenic agent (e.g., an alkaloid), and an agent blocking the growth of a cancerous tumor (such as a tyrosinase inhibitor or a monoclonal antibody).

The RNA according to the invention (possibly comprised or expressed using another product according to the invention described in this text) and the other active compound or compounds can be administered simultaneously, if applicable in a same composition, or sequentially.

The products of the invention (nucleic acid sequences, vectors, cells, compositions) can be adapted for intravenous, oral, sublingual, parenteral, rectal, topical, transdermal, subcutaneous, mucosal, intramuscular, intrapulmonary, intranasal, vaginal, etc., administration according to standard protocols well known to the person skilled in the art.

Preferably, the product is adapted for oral administration and presented in a solid or liquid form. The product can be in the form of a food, tablet, capsule, pill, dragee, lozenge, granules, or oral solution. In the case of parenteral administration, it is preferably in the form of a liquid solution, an emulsion or a suspension. In the case of intravenous, intradermal or subcutaneous administration, it is typically in the form of a solution for injection.

The nucleotide sequence of interest can also be administered by electroporation, into the muscles or through the skin of the subject.

The dosage (or therapeutically-effective quantity) is easily determined by the skilled person so that the desired effects (i.e., extending the lifespan, fighting the harmful effects of aging, stress and/or infertility) are attained. The specific dose of the product should be adjusted to the subject concerned and the desired application. It depends on several factors, including the weight, health status, sex and diet of the subject, the administration route, absorption and excretion rates, and possible combination with one or more other active molecules.

The total daily dose of the product administered to a human subject in a single dose or in several doses may be, for example, comprised between 1 µg and 20 mg per kilo, preferably between 100 µg and 5 mg. The administrations can be weekly or daily or even repeated several times a day. The RNAs or compositions according to the invention comprising them can be administered in the form of a unit dose comprising 0.05 to 20 mg of RNA, preferentially 0.1 to 5 mg.

In one particular embodiment, an RNA sequence of interest of the invention is used in a therapeutic composition, for example a vaccine.

In another particular embodiment, an RNA sequence of interest of the invention is used in a cosmetic composition.
Applications of the Products of the Invention The present invention concerns in particular a product such as described in this text consisting of, or comprising, an RNA sequence or a DNA sequence of interest according to the invention for use as a medicament.

It also concerns a product or composition according to the invention for use i) to prevent or treat a pathology, an abnormality, a disorder or an apparent or functional deterioration related to a mechanism of aging, ii) to extend the lifespan of a subject, or iii) to increase the resistance of a subject to a stress.

In one particular aspect, the present invention relates to the use of such a product in a therapeutically-effective quantity for the preparation of a pharmaceutical composition intended i) to prevent or treat a pathology, an abnormality, a disorder or an apparent or functional deterioration related to a mechanism of aging, ii) to extend the lifespan of a subject, or iii) to increase the resistance of a subject to a stress.

In still another particular aspect, the present invention concerns the use of such a product for the preparation of a cosmetic composition.

The term "treatment" as used in this document refers to improvement or resolution of symptoms, slowing the progression of the disease or aging process, stopping the progression of the disease or resolution of the disease.

The inventor has demonstrated the surprising efficacy of the RNA sequences according to the invention in delaying aging process(es) and fighting pathologies and harmful effects associated with these process(es).

The inventor has notably demonstrated that the overexpression in *Drosophila* of snoRNA:Ψ28S-1153 of SEQ ID NO: 1 spectacularly doubles the lifespan of said *Drosophila*. In particular, they demonstrated that mutant flies for snoRNA:Ψ28S-1153 have more neurodegenerative lesions than wildtype flies at 40 days old (FIG. 12). In general, flies overexpressing snoRNA:Ψ28S-1153 have fewer, or even no brain lesions, which shows the protective nature of the snoRNA according to the invention relative to neurodegenerative pathologies. Furthermore, the inventor has shown that 40-day-old flies overexpressing snoRNA:Ψ28S-1153 have better sensorimotor performances (represented here by the distance travelled during a test quantifying locomotor activity) than wildtype flies and are therefore protected from the harmful effects associated with mechanisms of aging (FIG. 13).

The inventor has demonstrated that the overexpression of an RNA sequence of interest according to the invention permits extending the life of a subject, delaying the mechanisms of aging and fighting the harmful effects associated with these mechanisms. In particular, they showed that this overexpression is neuroprotective and serves in particular to prevent or treat a degenerative disease, in particular neurodegenerative, typically neurodegenerative diseases associated with accumulation of iron, which result in demyelination in the brain, such as, neurodegenerative diseases caused by one or more mutations of the fa2h gene. The invention also particularly permits treating leukodystrophies (typically those related to mutations of the fa2h gene) or hereditary spastic paraplegia (typically SPG35 hereditary spastic paraplegia). It also permits preventing or treating diabetes, cancer, or fertility or sterility problems (FIG. 14), and also favors maintenance of the locomotor activity of the treated subject.

"Subject" means any living being that could benefit from such a treatment, regardless of its sex or age. Preferably, the subject is an adult subject. The subject may be an insect such as a *Drosophila*, or an animal, for example a mammal (preferably a primate or a human being) or a rodent (preferably a mouse or rat).

Preferably, the subject i) does not express the RNA sequence of interest or expresses an abnormal version of said RNA sequence, ii) is experiencing conditions of stress (particularly a subject having reached sexual maturity, preferably an elderly subject) such as fasting, heat shock, oxidative stress (such as paraquat exposure) or a stress (in the intestine) responsible for a detectable cellular proliferation or deregulation of the Delta/Notch pathway, and/or iii) is suffering from a disease related to or promoted by aging, typically a degenerative disease, in particular neurodegenerative, a laminopathy such as progeria, obesity, diabetes, cancer or fertility problems (particularly including infertility or sterility).

In a particular embodiment, the genome of the subject likely to benefit from the invention i) does not express an RNA sequence of interest as described in this text, ii) expresses an abnormal version of said RNA sequence of interest, or iii) contains a DNA sequence comprising a mutation responsible for the non-expression or abnormal (i.e., non-functional) expression of said RNA sequence of interest.

The normal (wildtype) version of the DNA sequence can be chosen, for example, from SEQ ID NO: 5, SEQ ID NO: 6, SEQ ID NO: 7, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28 and SEQ ID NO: 30, identified previously. A mutation likely to affect the normal version of the DNA sequence, i.e., to impede the expression of an RNA sequence of interest according to the invention, is typically chosen from among a deletion, an addition and/or a substitution of one or more nucleotides.

The term "longevity" or "lifespan" refers to the lifespan for which a subject is programmed as a biological species, living under ideal conditions and in the absence of disease or accident. "Maximum longevity" or "maximum lifespan" is the maximum lifespan the individual of a given species can attain. For practical purposes, the maximum longevity of a subject is estimated by the maximum age reached by one of the members of a population. "Mean longevity" or "mean lifespan" is the age to which 50% of a given population survives.

A widely-recognized method to measure the effect of a treatment on "extension of lifespan" is by reference to maximum longevity or mean longevity. If a treatment significantly increases the maximum or mean longevity of a group of subjects relative to a group of control subjects, then there is considered to be an extension of lifespan and delay of aging.

In *Drosophila*, sexual maturity is reached, on average, at the age of one day. The mean lifespan is around 30 days. The maximum lifespan is comprised between around 60 and 80 days depending on the *Drosophila* species and line and the living or rearing conditions. In mice, sexual maturity is reached, on average, 42 days after birth. The mean lifespan is around 832 days. In human beings, sexual maturity is reached between 9 and 14 years of age. The mean lifespan is 73 years for men and 79 years for women. The maximum lifespan is currently 122 years, 5 months and 14 days.

The term "aging" in the context of this invention is a process of gradual and spontaneous changes ranging from maturation, through childhood and puberty, up to functional decline of the subject. Aging therefore comprises the positive component of development and maturation and the negative component of decline.

The RNA sequences of interest of the invention increase the maximum or mean longevity (or lifespan) of a subject. Preferably, these sequences extend lifespan and delay aging of a subject or a subpopulation of adult subjects, defined, for example, by sex and/or age (i.e., by a minimum age or a maximum age or by an age window).

Using the present invention, extending the lifespan of *Drosophila* as well as mammals, including mice and, in particular, human beings, by around 50% or even 100%, while improving conditions of aging is typically considered.

Using the RNA sequences of the present invention, it is also possible to fight "the harmful effects of aging". In the context of the present invention, this expression means the negative component of aging, i.e., decline of the subject. Progressive decline, with age, of physiological capacities varies from one organ to another and from one subject to another. The physiological decline of a subject leads to a reduced ability to respond to environmental stimuli and an increase in susceptibility and vulnerability to diseases and impairments. The harmful effects of aging encompass the accumulation of undesirable changes that have an impact on weakening a given subject and that can precipitate its death. These changes may be attributed to development, to innate aging processes, to possible genetic abnormalities, to the environment and to diseases that affect or did affect the subject.

Moreover, using the present invention, it is possible to prevent or treat degenerative diseases, in particular neurodegenerative, typically degenerative diseases affecting the central and/or peripheral nervous system.

In a preferred embodiment, the invention permits preventing or treating neurodegenerative diseases associated with the accumulation of iron leading to demyelinization in the brain, in particular neurodegenerative diseases induced by one or more mutations of the fah2 gene. The invention therefore permits treating leukodystrophies (typically those linked to mutations of the fa2h gene) or hereditary spastic paraplegia (typically SPG35 hereditary spastic paraplegia).

In other embodiments, the invention will prevent or treat a pathology selected from among myopathy, Hunter syndrome, dyskeratosis congenita, Prader-Willi Syndrome, Alzheimer's disease, Parkinson's disease, Huntington's disease, multiple sclerosis and amyotrophic lateral sclerosis (ALS).

In another embodiment, the present invention will prevent or treat laminopathies such as Hutchinson-Gilford syndrome (or progeria), mandibuloacral dysplasia (MAD), Emery-Dreifuss muscular dystrophy, atypical Werner syndrome, restrictive dermatopathy, lethal fetal akinesia, and LIRLLC (Generalized lipoatrophy, insulin-resistant diabetes, leukomelanodermic papules, liver steatosis, and hypertrophic cardiomyopathy), preferably Hutchinson-Gilford syndrome.

In yet another embodiment, the present invention will prevent or treat diabetes or obesity.

It may also participate in the prevention or treatment of cancer or neoplastic process. The cancer is typically a cancer selected from among carcinoma, sarcoma, lymphoma, melanoma, pediatric tumor or leukemia. It may, for example, be breast cancer, ovarian cancer, endometrial cancer, prostate cancer, esophageal cancer, colon cancer, rectal cancer, kidney cancer, lung cancer, thyroid cancer, osteosarcoma, melanoma, leukemia, neuroblastoma, etc.

In one particular embodiment, this invention is particularly useful to fight cancer induced by free radicals such as colon cancer and stomach cancer.

It is also possible to fight problems of infertility or sterility using the product according to the invention. "Infertility" or "sterility" means difficulty conceiving or inability to conceive. In the context of this use, the subject is typically female, sexually mature and having difficulty, for example premature, reproducing. Typically the subject is sterile, infertile or has had an early or premature reduction in fertility. The RNA sequences of interest according to the invention allow treating infertility or restoring, increasing, enhancing or stimulating the fertility of the treated subject.

The present invention also concerns a method for treating a pathology, abnormality, disorder, harmful effect or apparent or functional deterioration related to a mechanism of aging or to a stress, such as described in this text.

Methods Permitting Evaluating the Preventative or Therapeutic Efficacy of a Test Compound The invention also provides a method for evaluating the cosmetic or therapeutic efficacy of a test compound to fight the harmful effects of aging or a stress as well as against the pathologies associated with such a stress or such a mechanism of aging or for fighting infertility.

"Test compound" means any compound potentially involved in the fight against the harmful effects of aging, against a stress or against infertility. For example, it can be a natural or chemical molecule, a metal, an irradiating agent, etc.

A compound can be tested for its potential therapeutic efficacy, i.e., its ability to prevent, treat or enhance the treatment of diseases and harmful effects of aging or a stress, e.g., laminopathy, a degenerative disease or a cancer as described previously, to prevent, treat or enhance the treatment of diabetes or obesity, or to prevent, treat or enhance the treatment of infertility.

A compound can also be tested for its potential cosmetic efficacy, i.e., its ability to improve the physical appearance of the subject and better fight an apparent deterioration of the subject related to a mechanism of aging. The test compound can prove effective, for example, in the cosmetic treatment of the epidermis, body hair and/or capillary system, nails, lips, external genital organs, teeth or mucosa.

In a first embodiment, the method described in the invention comprises the following steps:
i) exposure of a cell, a population of cells or a tissue not expressing the RNA sequence according to the invention or expressing an abnormal version of said RNA sequence, or a transgenic mouse according to the invention,
ii) evaluation of the effects, if any, of the test compound on the phenotype of said cell(s) or said tissue or said transgenic mouse, and
iii) determination of the cosmetic or therapeutic efficacy of said test compound, a restoration of the activity and/or expression of said RNA sequence being correlated with an efficacy of said test compound.

The cosmetic or therapeutic efficacy of said test compound can be evaluated or determined in reference to a control value. This control value can be established from the level of activity and/or expression of said RNA sequence in a cell, a population of cells or a tissue not expressing or expressing an abnormal version of said RNA sequence or in a transgenic mouse according to the invention.

If the activity and/or expression of said RNA sequence present in the cell, population of cells, tissue or transgenic mouse exposed to the test compound is greater than the activity and/or expression of the RNA sequence in the cell, population of cells or tissue not expressing or expressing an abnormal version of said RNA sequence or in said transgenic mouse of the invention, then the test compound has cosmetic or therapeutic efficacy.

In a second embodiment, the method described in the invention comprises the following steps:
i) exposure of a cell according to the invention comprising an RNA sequence according to the invention, a population of cells or a tissue comprising a cell according to the invention,
ii) evaluation of the effects, if any, of the test compound on the phenotype of said cell or population of cells or said tissue, and
iii) determination of the cosmetic or therapeutic efficacy of said test compound, an increase of the activity and/or expression of said RNA sequence being correlated with an efficacy of said test compound.

According to this aspect of the invention, a control value can be established from the level of activity and/or expression of said RNA sequence in a cell or a population of cells expressing said RNA sequence.

In this case, if the activity and/or expression of said RNA sequence present in the cell or population of cells exposed to the test compound is greater than the activity and/or expression of the RNA sequence in the cell or population of cells expressing said RNA sequence, then the test compound has cosmetic or therapeutic efficacy.

The level of activity and/or expression of the RNA sequence can be quantified using techniques known to the skilled person, typically by quantitative PCR or immunohistochemistry (staining by antibodies directed against the genes/proteins regulated by the snoRNA of interest).

The therapeutic effect can also be evaluated, for example, by determining the lifespan of the cells, by measuring the number of cell divisions, etc.

Preferably, the cell or population of cells exposed to the test compound is of intestinal or ovarian origin. Preferred cells can be chosen from among the cells mentioned in this text, typically from among enteroblasts, enterocytes, enteroendocrine cells, intestinal stem cells, nurse cells, typically nurse cells of the ovarian chamber, oocytes, ooblasts, etc.

Other aspects and advantages of the present invention will appear upon reading the figures and examples that follow, which should be considered as illustrative and non-limiting.

BRIEF DESCRIPTION OF THE FIGURES

The patent or application file contains at least one drawing executed in color. Copies of this patent or patent application publication, with color drawing(s), will be provided by the Office upon request and payment of the necessary fee.

FIG. 2A: H/ACA box motif; FIG. 2B: Pseudouridylation diagram. (Extract from Kiss et al. (2010) *Molecular Cell*, 37, 597-606).

FIG. 4A, Heat Shock: The F4 mutants are more resistant than the controls (females only). Flies overexpressing the snoRNA (G5), as well as F4 mutants provided with the transgene (F4;G5) are more resistant than the controls (males and females).

FIG. 4B, Fasting: The F4 mutants are more resistant than the controls (males and females). Flies over-expressing the snoRNA (G5) are more resistant (females only). F4 mutant female flies provided with the transgene (F4;G5) are similar to the control flies; therefore the wildtype is restored by the transgene.

FIG. 4C, Paraquat: The F4 mutants are more resistant than the controls (males and females). Flies over-expressing the snoRNA (G5) are more resistant (females only). F4 mutant flies provided with the transgene (F4;G5) are similar to the control flies, therefore the wildtype is restored by the transgene.

FIG. 5A: In the wildtype control mice (Canton-S), the snoRNA is expressed in the epithelial cells of the intestine. Blue: DNA staining in the nucleus by DAPI. Red: snoRNA staining. Note that the snoRNA staining (red points) is distinct and complementary to that of the nucleus (blue), demonstrating that this latter is localized in the nucleolus.

FIG. 5B: In the F4 mutant (deletion of the snoRNA), the blue staining is seen (DAPI) but no red staining, because the snoRNA is deleted and therefore not expressed.

FIG. 5C: Control flies, wildtype (Canton-S). The snoRNA is expressed in ovarian nurse cells.

FIG. 5D: F4 mutant flies. The snoRNA is not expressed in the ovaries.

FIG. 6A) Targeted expression of the snoRNA in enterocytes, under the control of Myo1A-Gal4 (Myo1A-Gal4; UAS-mCD8-GFP). FIG. 6B) Targeted expression in enterocytes by Myo1A-Gal4, in the F4 mutant genetic background (Myo1A-Gal4, F4/F4; UAS-snoRNA-8M/+). FIG. 6C) Targeted expression in the intestine under the control of esg-Gal4 (esg-Gal4, UAS-GFP) staining intestinal stem cells (ISCs). FIG. 6D) Targeted expression in the intestine under the control of Su(H)-Gal4 (Su(H)-GBE-Gal4; UAS-mCDB-GFP), staining enteroblasts. FIG. 6E) Targeted expression in the intestine under the control of Delta-Gal4 (D1-Gal4, UAS-GFP) staining intestinal stem cells (ISCs).

FIG. 7A: Targeted expression under the control of esg-Gal4 (esg-Gal4, F4/F4; UAS-8M/+)

FIG. 7B: Targeted expression under the control of Su(H)-Gal4 (Su(H)-GBE-Gal4, F4/F4; UAS-8M/+).

FIG. 7C: Targeted expression under the control of Delta-Gal4 (Delta-Gal4, F4/F4; UAS-8M/+).

FIG. 8A, Fasting: Targeted expression of the snoRNA (UAS-8M) under the control of Myo1A-Gal4. There is a clear increase in resistance in flies expressing the snoRNA (Myo, F4/F4; 8M/+) relative to the two control lines.

FIG. 8B, Fasting: Targeted expression of the snoRNA (UAS-8M) under the control of esg-Gal4. There is a clear increase in resistance in flies expressing the snoRNA (esg, F4/F4; 8M) relative to the two control lines.

FIG. 8C, Fasting: Targeted expression of the snoRNA (UAS-8M) under the control of Su(H)-Gal4. There is a clear increase in resistance in flies expressing the snoRNA (Su(H), F4/F4; 8M) relative to the two control lines.

FIG. 8D, Heat shock at 36° C.: Targeted expression of the snoRNA (UAS-8M) under the control of Su(H)-Gal4. There is a clear increase in resistance in flies expressing the snoRNA (Su(H), F4/F4; 8M) relative to the two control lines.

FIG. 9A: Homologies in the twelve species of *Drosophila* whose genome is known (Dmel, SEQ ID NO: 38; Dsim, SEQ ID NO: 39; Dsec, SEQ ID NO: 40; Dyak, SEQ ID NO: 41; Dere, SEQ ID NO: 42; Dana, SEQ ID NO: 17; Dpse, SEQ ID NO: 19; Dper, SEQ ID NO: 21; Dwil, SEQ ID NO: 23; Dmoj, SEQ ID NO: 25; Dvir, SEQ ID NO: 27; Dgri, SEQ ID NO: 29)

FIG. 10: Human homolog on chromosome 11 (Dmel-psi28S1153, SEQ ID NO: 38; hg18-chr11_12822722-12822880, SEQ ID NO: 2).

FIGS. 11A-11B: 2 homologous genes in *Mus musculus* (FIG. 11A, mouse-1 (Dmel-psi28S1153, SEQ ID NO: 38; mm9-chr15_30336889-30337017, SEQ ID NO: 3) and FIG. 11B, mouse-2 (Dmel-psi28S1153, SEQ ID NO: 38; mm9-chr18_6495012-6495133, SEQ ID NO: 4)).

FIG. 13A) Distance travelled by females. FIG. 13B) Distance travelled by males.

FIG. 15A: Model of intestinal epithelium regeneration in the adult *Drosophila*.

FIG. 15B: Model of the Notch function in entero-endocrine cells in the *Drosophila* (embryo, larva, pupa, adult) and in mammals. Dl=Delta, N=Notch, NO=no Notch signal. This diagram clearly shows the perfect similarity between the intestinal epithelium of *Drosophila* and that of humans.

FIGS. 18A-18B: The youth snoRNA is involved in RNA level regulation of two other genes: klarsicht and gene CG30502 (fa2h). FIG. 18A) For klarsicht, amplification of a 464-bp fragment (comprised in an exon) shows that there is less product transcribed in the F4 mutant than in wildtype control flies (Canton-S). FIG. 18B) For fa2h, amplification of a 429-bp fragment (comprised in an exon) shows that there is less transcribed in the F4 mutant than in wildtype control flies (Canton-S).

FIG. 19A) klarsicht, via its KASH domain, interacts with the lamina, located on the internal surface of the nuclear membrane (according to Patterson et al., 2004). FIG. 19B) Schematic view showing the structure and function of nuclear lamins. The lamins are located on the internal surface of the nuclear membrane and serve to maintain the stability of the nucleus, organize chromatin and bind nuclear pores (NPC). Several proteins interacting with the lamins are also diagrammed (according to Coutinho et al., Immunity & Ageing, 2009).

EXPERIMENTAL PART

1) Genetic and Molecular Characterization of snoRNA: Ψ28S-1153 (Youth) Located at Locus P[GAL4]4C.

Figure 1:
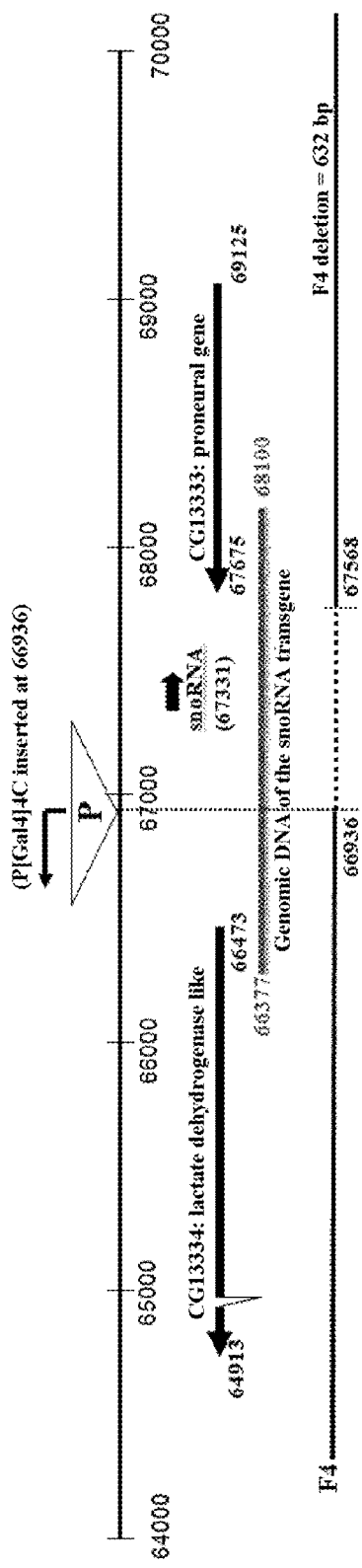
FIG. 1: Map of the genomic region of locus P[Gal4]4C, position of the youth snoRNA and the F4 deletion.
Figure 2A:
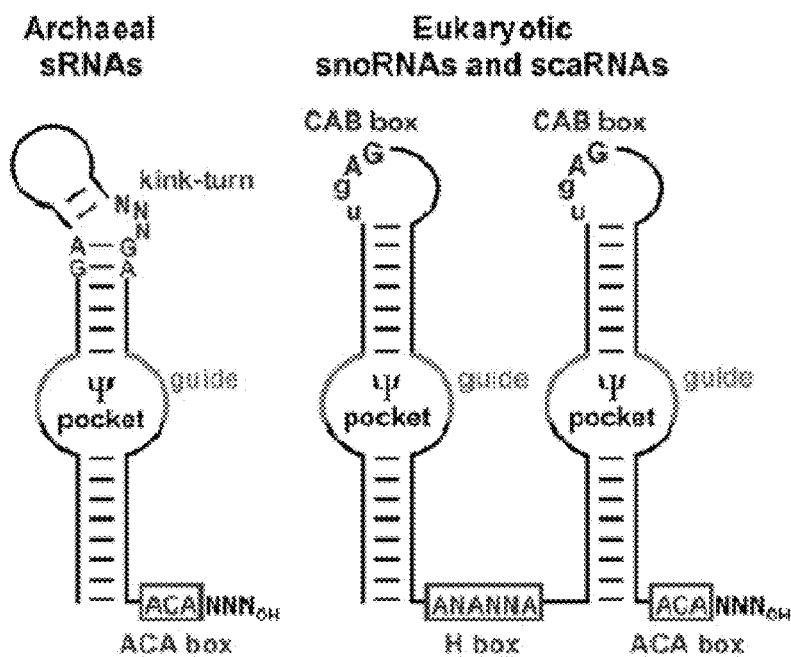
FIGS. 2A-2B.
Figure 2B:
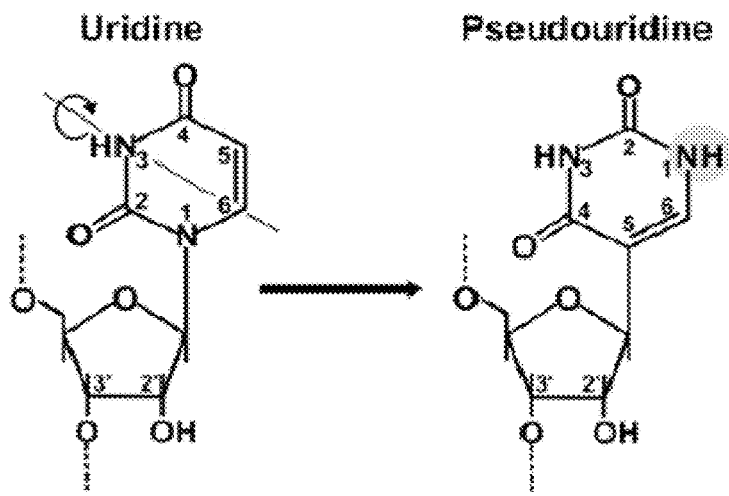

This experiment is part of the search for the neural basis involved in locomotor behavior in *Drosophila* and the study of the relationship between structure and function of the central complex and especially the ellipsoid body. In this context, screening a library of P[GAL4] enhancer trap lines permitted identifying the P[GAL4]4C line that is specifically expressed in the ellipsoid body (FIG. 1). Different genetic approaches, notably the targeted expression of tetanus toxin, have shown that blocking these neurons generates defects in locomotor activity (Martin et al., 2002). In a second step, in order to further characterize these neurons in detail and better determine their function within the neural network involved in locomotor activity, the insertion locus of the P[GAL4]4C line was characterized genetically and molecularly. PCR-rescue was done and permitted showing the insertion point of the P-element of P[GAL4]4C on chromosome 2R (Right: i.e., on the right arm), in position 50A, between two genes, CG13333 and CG13334 (FIG. 1). Then, in order to be able to show the respective phenotype and function of these two genes, mutations were generated in them by re-excision of the P-element (by a genetic approach called jump-out, or revertant). A small deletion of 632 base pairs (bp) named F4 was thus obtained (FIG. 1).

snoRNA:Ψ28S-1153 was identified at this locus in position 67331 (FIG. 1) as part of the systematic screening done by Huang et al. (2005) of all the potential small nucleolar RNA (snoRNA) in the *Drosophila* genome. The corresponding article, however, does not distinguish any particular snoRNA and does not associate any function with snoRNA: Ψ28S-1153. In the context of the present invention, this snoRNA, absent the small F4 deletion, has been precisely positioned and characterized structurally and functionally.

This snoRNA is thus made up of 148 base pairs (bp) and its structure comprises an H/ACA box.

2) Phenotypic Characterization of the F4 Deletion: Reduction of Lifespan.

Figure 3:
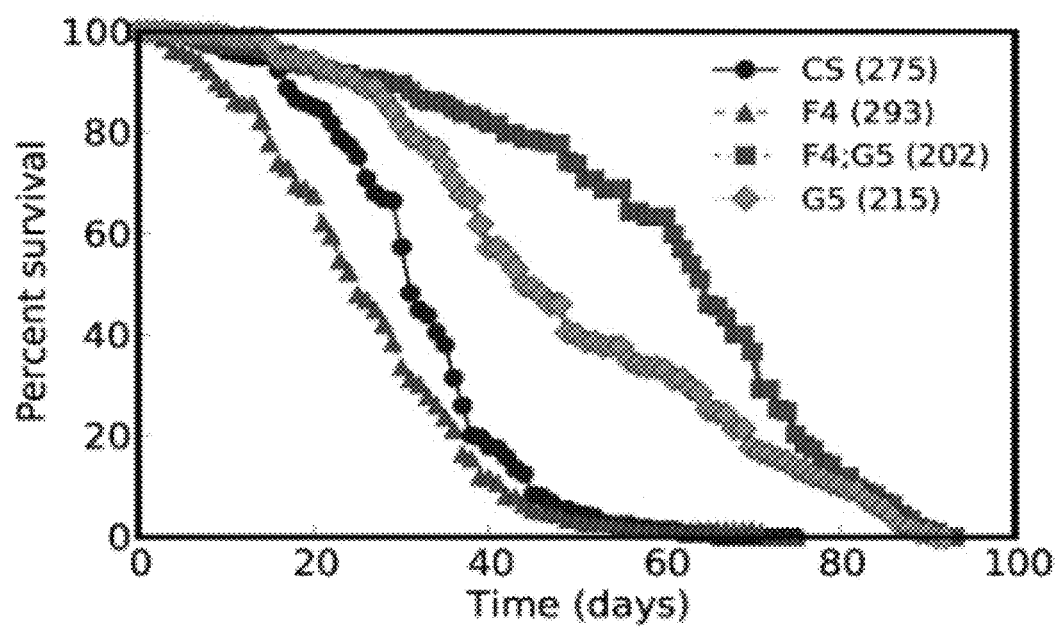
FIG. 3: Longevity of female flies. Cumulative decrease (in %) of the number of living flies as a function of the number of days. Cont–CS=wildtype control flies. F4=F4 mutant, G5=flies bearing the G5 genomic snoRNA transgene, F4;G5=flies bearing the G5 snoRNA transgene in the F4 mutant genetic background, to restore the wildtype phenotype (in parentheses: the number of flies).

At the same time as the study done to quantify the locomotor activity of the flies via the targeted expression of tetanus toxin in labelled ring neurons of the P[GAL4] 4C line, the inventor observed that these flies had a very short lifespan and decided to precisely quantify said lifespan of the P[GAL4]4C/UAS-tetanus-toxin flies, as well as that of the F4 flies (mutated at locus 4C). Thus the F4 flies have a short lifespan (of around 30% relative to wildtype control flies), suggesting that the snoRNA deletion could affect lifespan (longevity) (FIG. 3). The inventor also observed that this effect is different according to the sex of the flies, the effect being much more pronounced in females than in males.

3) Genesis of a Transgenic Line Containing the Genomic Region of the snoRNA (Youth) for Purposes of Restoring the Wildtype Phenotype ("Rescue").

In order to demonstrate that the phenotype of the F4 mutant is actually due to the deletion of the snoRNA, a line of transgenic *Drosophila* bearing a genomic DNA sequence of 1723 bp of the region (from 66377 to 68100), comprising the snoRNA (FIG. 1) and its regulator sequences, was generated. More precisely, a genomic fragment from the 1723-bp region was amplified by PCR and inserted via the Xba1 restriction site into the pCaSper-4 vector (this vector not containing any promotor/regulator sequence). Transgenic flies were then generated according to a standard technique and lines of flies expressing the same transgene, but inserted in distinct places of the genome, were obtained (independent insertions: G4, G5).

Next, in order to verify that the transgene is functional and can rescue the F4 mutation (i.e., restore the wildtype phenotype, that is restore a lifespan equivalent to that observed with no F4 deletion), the inventor introduced these transgenic lines in the context of the F4 genetic mutant, by standard genetic crosses (F4;G4 and F4;G5). It could thus be demonstrated that the transgene could rescue the phenotype due to the mutation responsible for the reduction in lifespan (FIG. 3) (see, for example: F4 versus F4;G5). Moreover, this transgene placed in a wildtype genome (normal) (which corresponds to an overexpression of this snoRNA, since there are now 4 copies of the snoRNA instead of the two endogenous copies) (G5) increases the lifespan (even doubles the lifespan in the case of F4;G5 or increases it by around 30% for G5) (FIG. 3). This experiment thus clearly shows that the lifespan of the animal can be increased by overexpressing this snoRNA (or by modifying its expression level). In summary, a small genomic deletion in the region (632 base pairs, called F4) (FIG. 1), corresponding or equivalent to mutation of this gene, shortened lifespan, while overexpression (via a transgene containing genomic DNA of this snoRNA) by gene therapy not only rescues the same mutation but dramatically extends (doubles) the lifespan of the subject treated (FIG. 3).

4) Stress Resistance Tests.

Figure 4A:
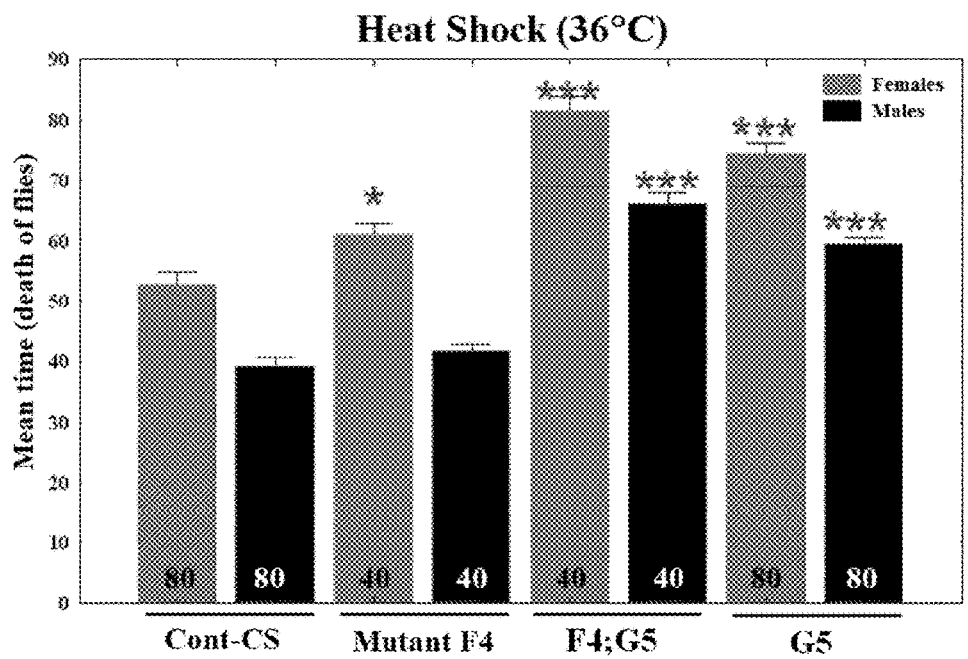
FIGS. 4A-4C: Stress resistance test (heat shock, fasting, paraquat) performed on three-day-old mice.
Figure 4B:
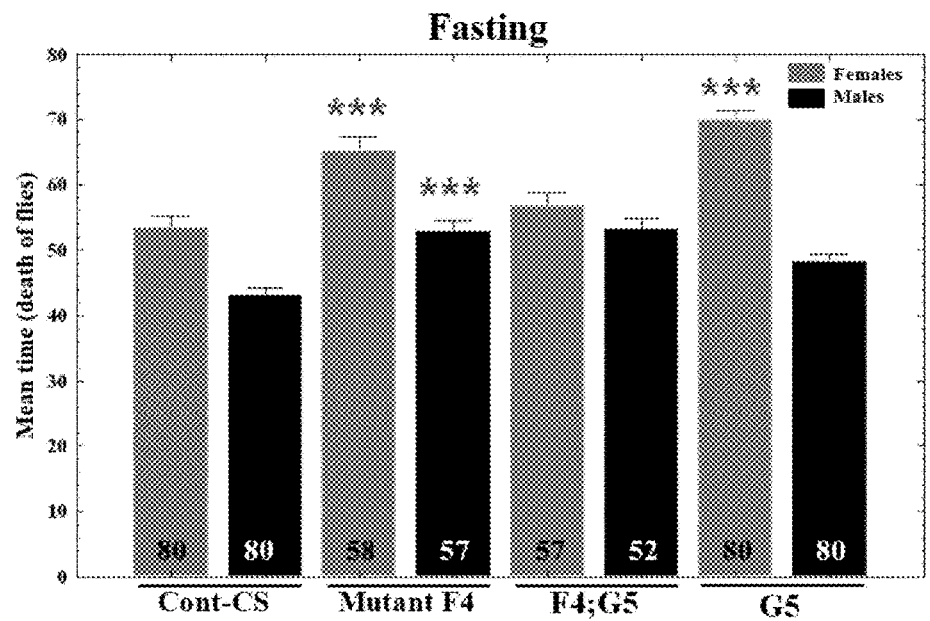

It is now generally acknowledged that genes acting on longevity generally increase stress resistance. The inventor has verified and obtained confirmation that overexpression of this snoRNA is effectively able to increase the lifespan of the subject concerned under stress conditions, such as fasting, heat shock and oxidative stress (induced by paraquat) (FIG. 4).

A) Heat Resistance Test (Heat-Shock Test).

Males and females are raised together in standard tubes containing feed for 3 days. At age 3 days, the males and females are distributed separately by group of 20 in a standard tube containing feed. To subject the flies to heat shock, tubes containing the flies are placed in an incubator at 36° C. The number of dead flies is counted every 6 hours. For heat shock (36° C.), in FIG. 4A, note that F4 mutant flies (females only) are more resistant than the control flies. However, the G5 flies (male and female) are more resistant than the controls and the F4 mutant, while as a result of the expression of the G5 transgene in the F4 mutant (F4;G5 flies) these flies are also much more resistant than the control flies and the F4 mutant flies.

B) Fasting Test.

Like the heat resistance test, males and females are raised together in standard tubes containing feed for 3 days. At age 3 days, the males and females are distributed separately by group of 20 into a tube containing a filter paper and 400 µL of water in order to prevent desiccation. The flies are kept in a humid room at 24° C., and the number of dead flies is counted every 6 hours. For fasting, in FIG. 4B, note that the F4 mutant flies (males and females) are more resistant than the control flies. Moreover, the G5 flies (female) are still more resistant, while the expression of the transgene in the F4 mutant (F4;G5) restores normal survival (in females).

C) Resistance to Oxidative Stress (Paraquat).

Paraquat (1,1'-dimethyl-4,4'-bipyridinium dichloride) reduces NADH, which generates stable paraquat radicals, which react with oxygen to generate ROS (reactive oxygen species). Consequently, the ROS cause cell damage (Rzezniczak et al., 2011). As in the previous tests, males and females are raised together in standard tubes containing feed for 3 days. At age 3 days, the males and females are distributed separately by group of 20 into an empty standard tube in order to fast them for 6 hours. Next, the flies are transferred into a tube containing a filter paper and 450 µl of 20 mM paraquat diluted in 1% sucrose to promote dietary intake. The flies are kept in a humid room at 24° C., and the number of dead flies is counted every 6 hours.

Figure 4C:
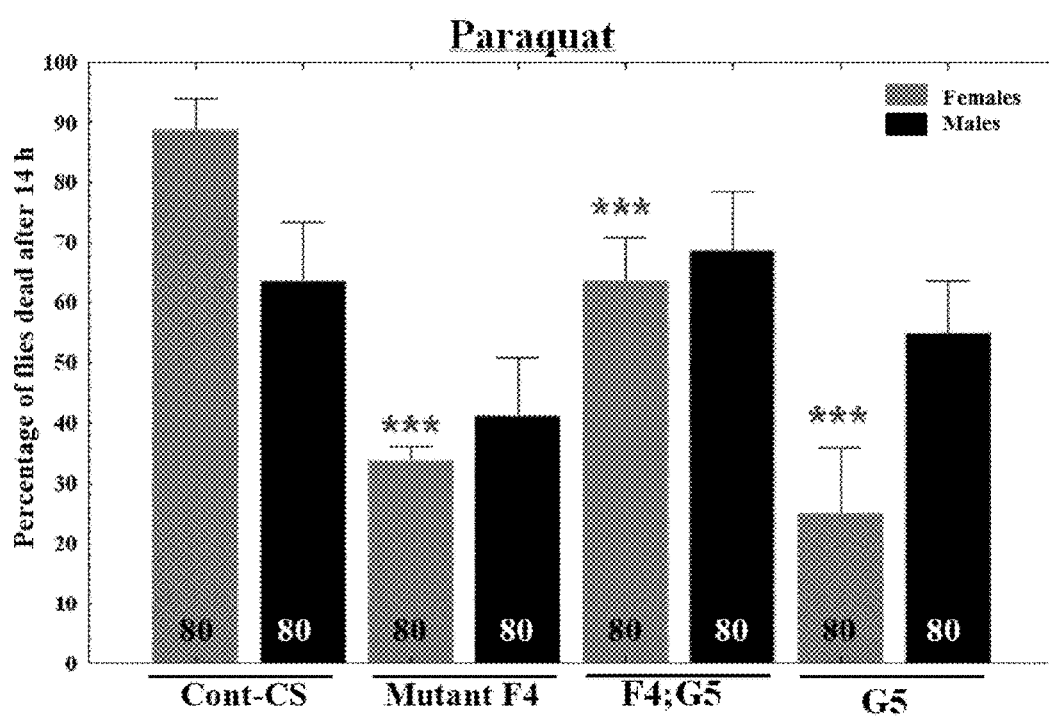

For oxidative stress, in FIG. 4C, note that the F4 mutant flies (females only, although there is also a strong trend for males) are more resistant than the control flies. Similarly, the female G5 flies are more resistant than the controls and similar to the F4 mutants, while the expression of the transgene in the F4 mutant (F4;G5) restores survival of the flies (equivalent to the control flies).

In summary, the F4 mutant flies are more resistant than the control flies, while overexpression (G5) further increases this resistance (an effect that is more marked and consistent in females than in males). Moreover, in both tests (fasting and oxidative stress) the expression of the transgene in the F4 mutant (F4;G5) restores fly survival, especially in females. Thus, contrary to longevity where the F4 mutation reduces lifespan, the F4 mutation increases resistance in the three stress tests done in young three-day-old flies, and this effect can be restored by the genomic transgene of the snoRNA (in two tests). In conclusion, modulation of expression (suppression, reduction or increase) of the "youth" snoRNA changes the lifespan of the subjects tested.

5) Determining the Space-Time Expression Profile of the snoRNA (In Situ Hybridization).

Figure 5A:
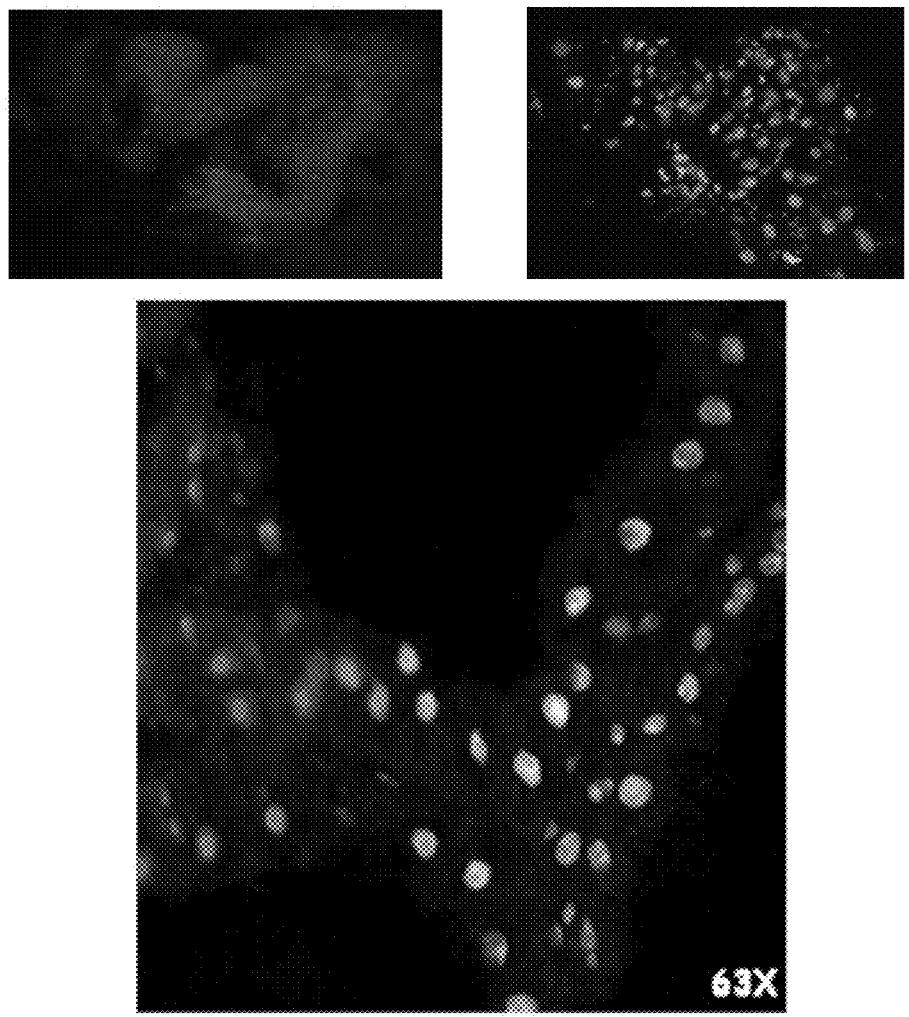
FIGS. 5A-5D: In situ hybridization in the intestine and ovaries.
Figure 5B:
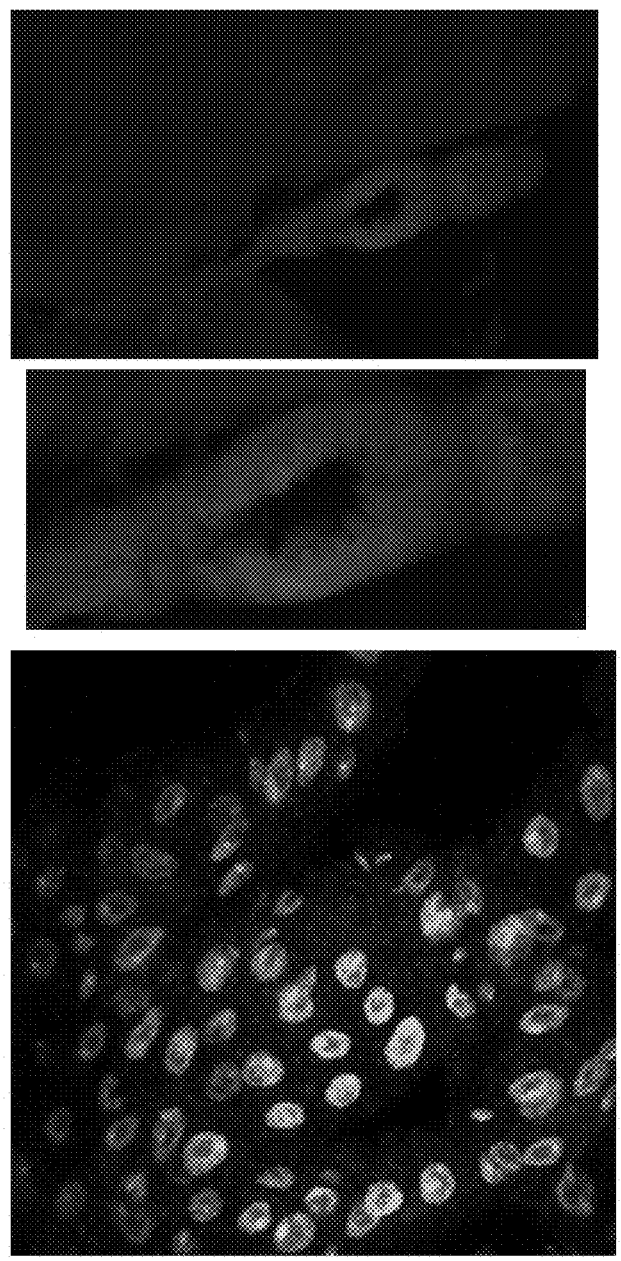
Figure 5C:
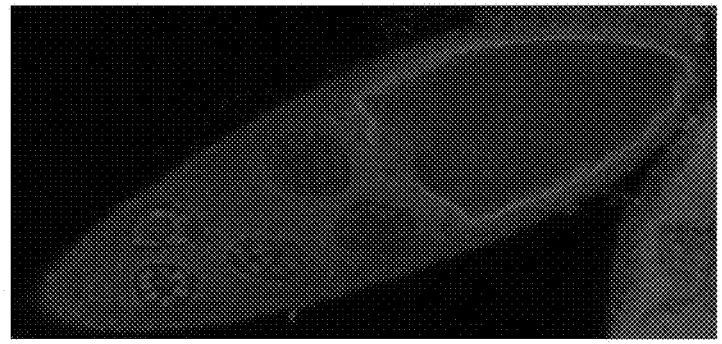
Figure 5D:
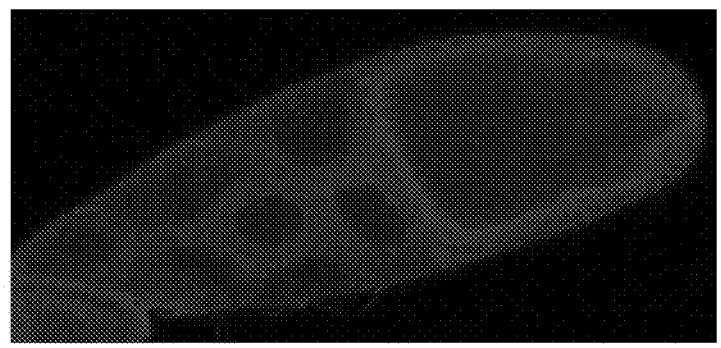
Figure 6A:
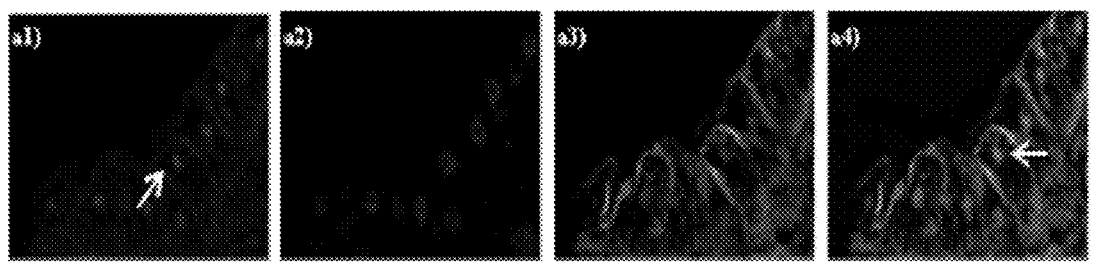
FIGS. 6A-6E: Targeted expression of the snoRNA in the epithelial cells of the intestine, via four separate Gal4 driver lines, driving the expression of a reporter gene GFP (UAS-GFP). Detection of the expression of the snoRNA by in-situ hybridization (red and/or orange) (left column: a1,b1,c1,d1, e1), staining of the nucleus with DAPI (blue) (second column: a2,b2,c2,d2,e2), expression of GFP by immunostaining (anti-GFP antibody revealed by FITC (green) (third column: a3,b3,c3,d3,e3). Right column (a4,b4,c4,d4,e4) superposition of the previous three images showing co-localization. Note that there is double staining only at (A) (Myo1A-Gal4), showing that the snoRNA is only expressed in the enterocytes.
Figure 6B:
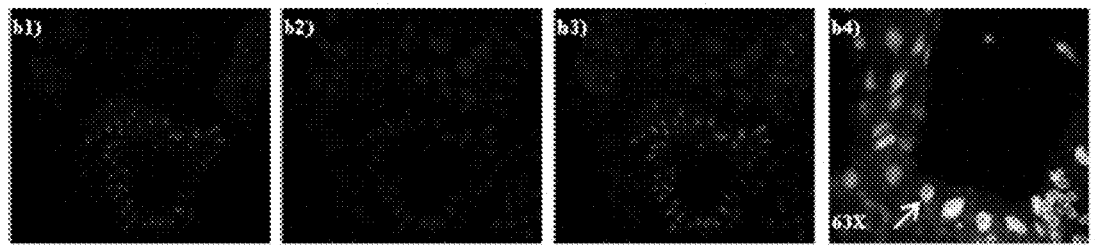
Figure 6C:
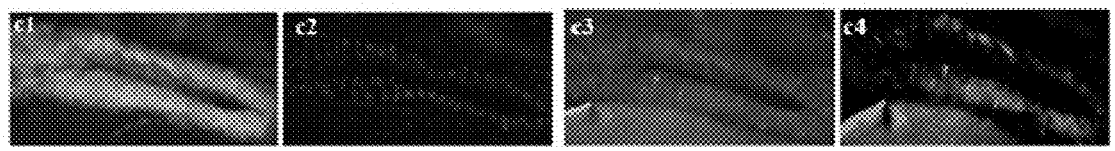
Figure 6D:
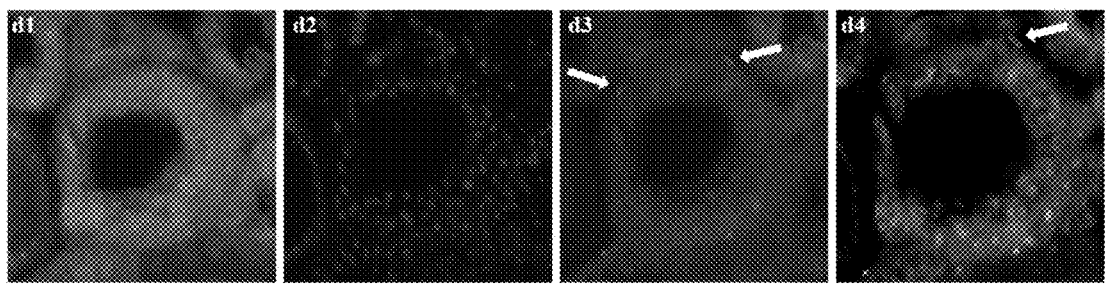
Figure 6E:
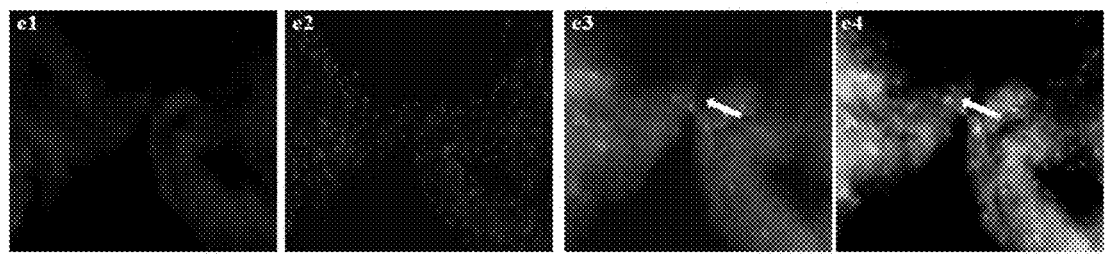

In order to determine in what cells and/or tissues the snoRNA of interest is expressed and acts, the space-time expression profile of this snoRNA was determined in the context of the invention, in the adult fly, by in situ hybridization (HIS), using an anti-sense snoRNA. Tyramide was used to amplify labelling. In both males and females, the youth snoRNA is expressed in the intestine wall (epithelium) (FIG. 5A), while, as expected, it is absent in the F4 mutant (FIG. 5B). More specifically, the use of P[Gal4] lines specific for various cell types of the intestine, combined with double labelling, demonstrated that the youth snoRNA is expressed specifically in the nucleolus of enterocytes, the main and majority cells forming the intestinal epithelium (FIG. 6A), while it is not expressed in other cell types (FIGS. 6B-6E). Furthermore, in females, it is also expressed in the ovaries, and more particularly in nurse cells (FIGS. 5C and 5D).

6) Targeted Expression of snoRNA in Cell Types Other than Intestine Epithelium.

Figure 7A:
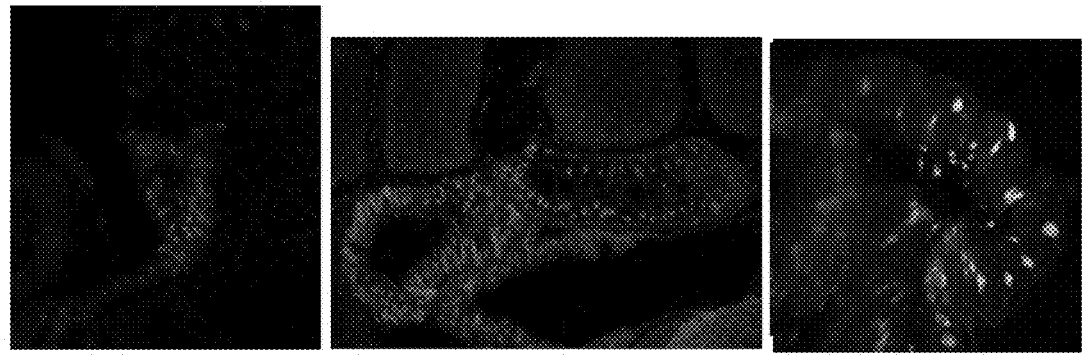
FIGS. 7A-7C: Targeted expression of the snoRNA in other cell types of the intestinal epithelium via three other separate Gal4 driver lines, driving the expression of the snoRNA (UAS-8M), demonstrating that the snoRNA can be expressed ectopically in other types of cells.
Figure 7B:
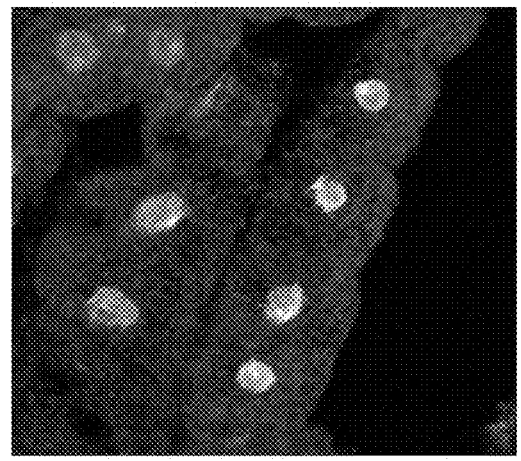
Figure 7C:
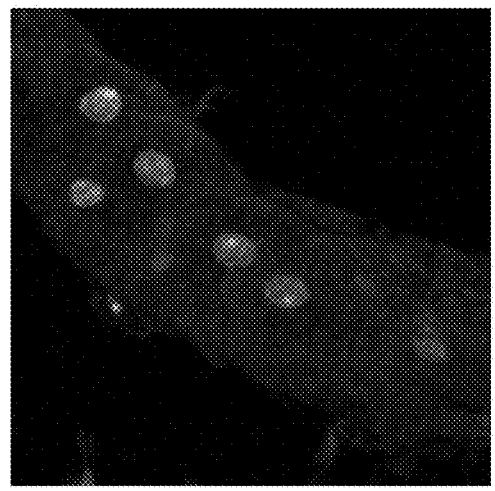
Figure 8A:
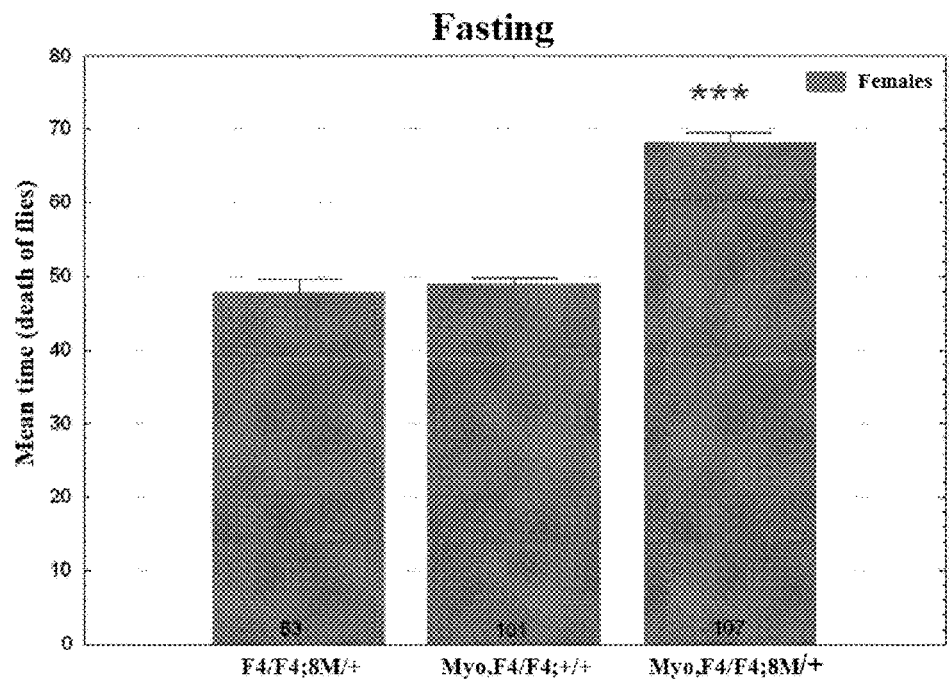
FIGS. 8A-8D: Resistance to various stresses following targeted expression (re-expression of the snoRNA in the F4 mutant genetic background) of the snoRNA in the intestines of three-day old flies.
Figure 8B:
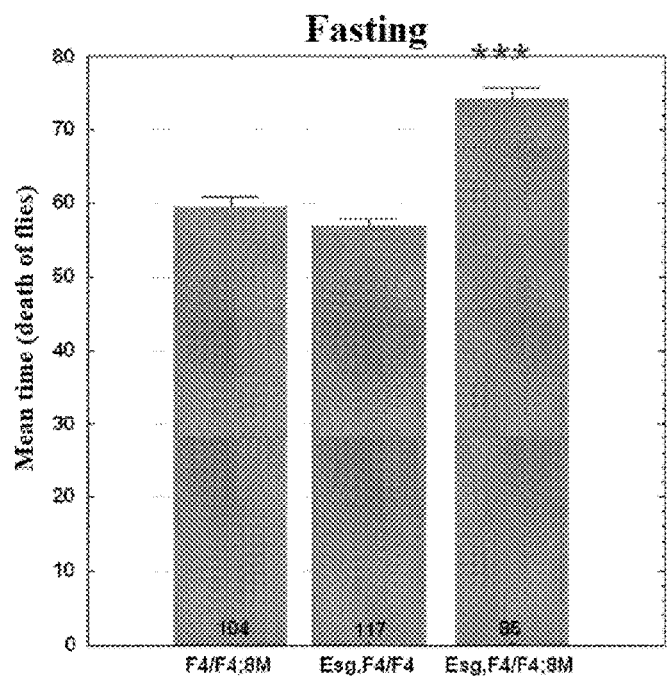
Figure 8C:
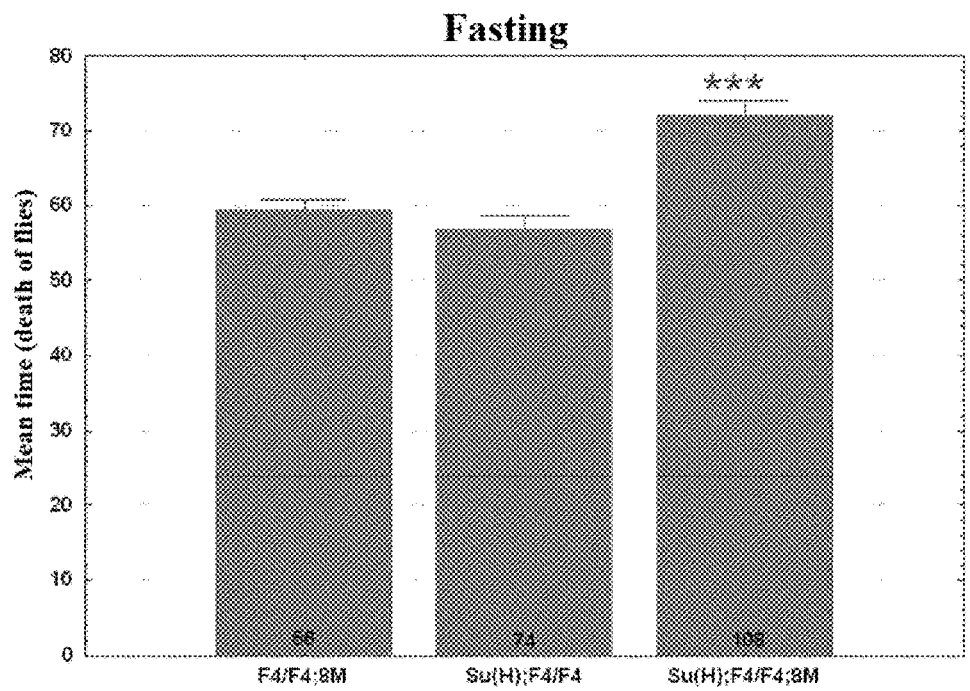
Figure 8D:
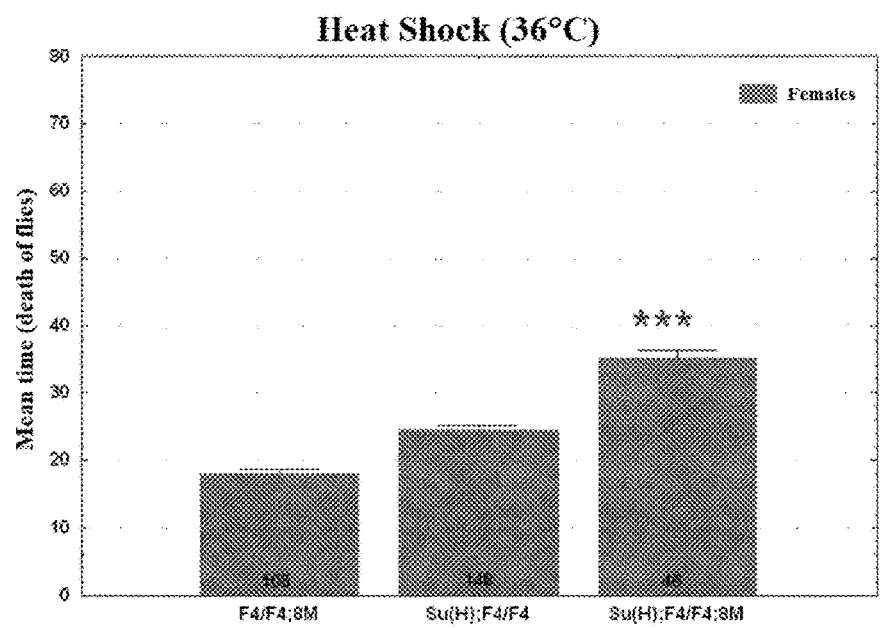

Targeted expression (ectopic) of snoRNA (UAS-8M) in types of cells other than intestine epithelium via the use of three other distinct Gal4 driver lines was done: esg-Gal4 (esg-Gal4, F4/F4; UAS-8M/+) and Delta-Gal4 (Delta-Gal4, F4/F4; UAS-8M/+) targeting intestinal stem cells (ISCs), while Su(H)-Gal4 (Su(H)-GBE-Gal4, F4/F4; UAS-8M/+) target enteroblasts (FIG. 7). These results demonstrate: 1) that the snoRNA can be expressed ectopically in other cell types, and 2) that this ectopic expression also increases the resistance to certain stresses (FIG. 8). In summary, these results show that the snoRNA can also confer protection when it is expressed in cell types other than intestine epithelium.

7) Targeted (Selective) Expression of the snoRNA Leading to Rescue of Stress Resistance.

The inventor has demonstrated, by two independent approaches, that a targeted expression in intestinal cells is sufficient to restore the stress resistance phenotype. It could be demonstrated, by the in situ hybridization technique, done from genomic transgenic lines (those increasing longevity: G5, as well with another independent insertion (G4)), that the snoRNA is expressed in intestinal cells and that, for regulation of longevity, the expression of the snoRNA in intestinal cells is sufficient.

In order to confirm this first result, the snoRNA was targeted only in intestinal cells, by using the P[Gal4] binary expression system. A plasmid vector (p[UAS-snoRNA]) was constructed in which the snoRNA of interest (only 148 bp) is placed under the control of regulator elements (Upstream Activating Sequence: UAS) of Gal4. Transgenic fly lines (UAS-snoRNA: 4M, 5M and 8M) were then generated. For targeted expression, so-called "driver" lines of transgenic flies containing a transgene (pChs-Gal4) (plasmid vector lines Myo1A-Gal4, esg-Gal4 (escargot-Gal4), Su(H)GBE-Gal4, and Dl-Gal4 (Delta-Gal4)), known to be expressed in particular in intestinal cells, were used (Jiang and Edgar, 2011; Takashima et al., 2011). Next, these various transgenes were placed in the F4 mutant genetic background, and it was demonstrated, by in situ hybridization, that the snoRNA is actually expressed in these various types of intestinal cells (FIGS. 6 and 7) after its targeted expression (esg-Gal4,F4/F4; UAS-snoRNA-8M) (Myo1A-Gal4,F4/F4; UAS-snoRNA-8M) (Su(H)-GBE-Gal4,F4/F4; UAS-snoRNA-8M) (F4/F4; Delta-Gal4/UAS-snoRNA-8M). The results show that this targeted expression (in the F4 mutant) substantially restores the stress resistance phenotype (fasting and heat shock) (FIG. 8).

These experiments clearly show that manipulating these snoRNAs in intestinal cells, and more particularly in enterocytes, is necessary and sufficient to restore stress resistance. These experiments, although conducted in Drosophila, permit suggesting that re-expression (restoration of expression or rescue) or overexpression of the snoRNA in epithelial cells of the intestine is able to lead to an increase in lifespan in mammals and in particular in humans.

8) Identification of Homologs of the Youth Sequence in Other Species of Drosophila and in Mammals, Including Mice and Humans.

Figure 9B:
FIG. 9B: consensus structure of the 12 species of *Drosophila* (SEQ ID NO: 43).

Sequence homology searching showed that these snoRNA also exist in the 11 other species of Drosophila whose genome is available (FIG. 9A) (see also the consensus structure of 12 species of Drosophila: FIG. 9B).

Moreover, a homology search, especially via the RNA structure (using INFERNAL software) allowed identifying a homolog in humans, located on chromosome 11, at positions 12822722-12822811 (FIG. 10). In mice, two homologs have also been identified: on chromosome 15, positions 30336889-30337017, and on chromosome 18, positions 6495012-6495091 (FIGS. 11A and 11B).

Like in Drosophila, it is very probable that the overexpression of this gene and/or a synthetic analog (either genetically or by oral administration, or by injection) will extend the human lifespan. Such expression is also able to protect against the harmful effects of various degenerative diseases.

9) Role of the snoRNA in Neuro-Degeneration and Neuro-Protection.

Figure 12:
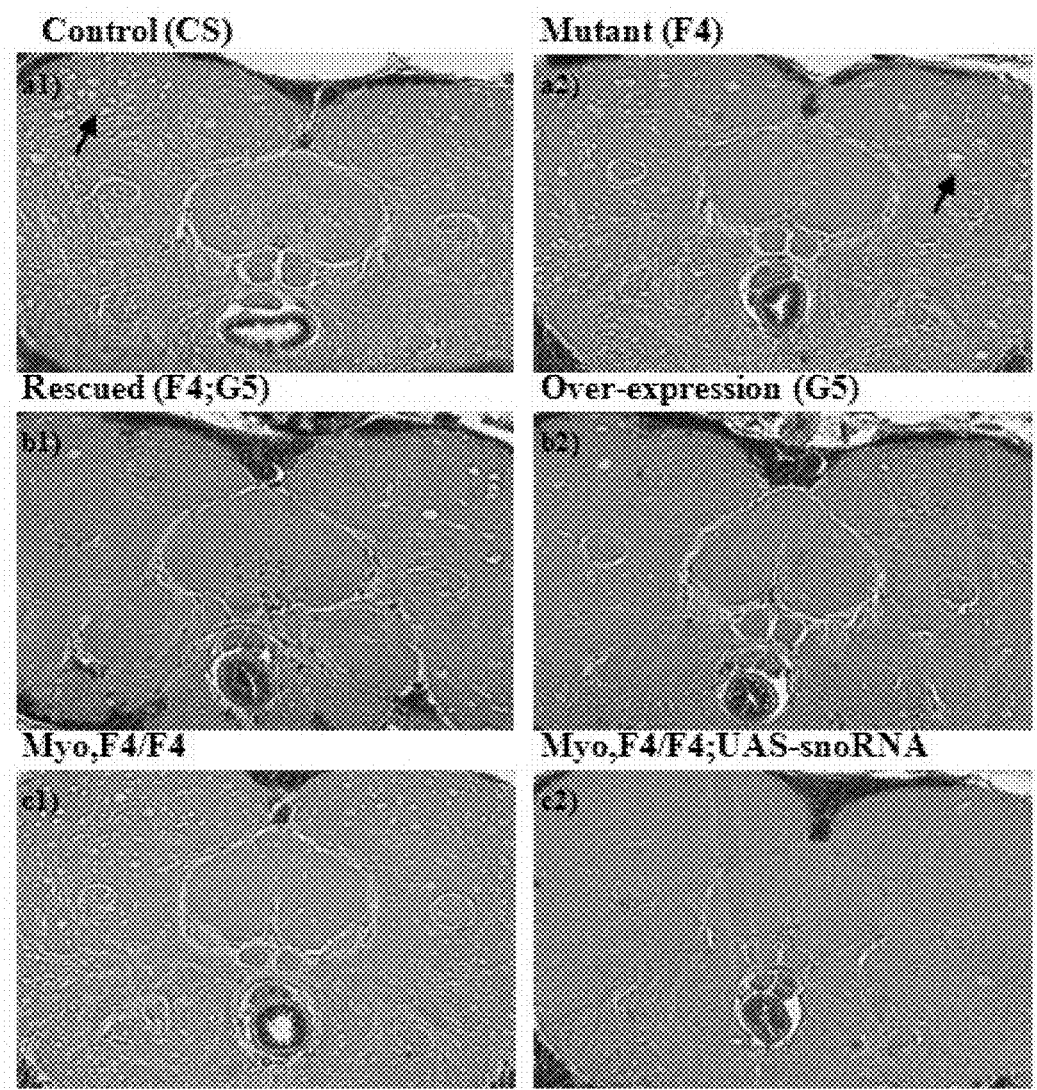
FIG. 12: Brain histology: visible neurodegeneration in the brain of 40-day-old flies. Control flies (Canton-S wildtype) (a1) present neurodegeneration lesions (vacuoles/gaps) while F4 mutant flies (a2) present more lesions. Flies expressing the snoRNA in the mutant genetic background (rescued: F4;G5) (b1) present fewer lesions than the CS and F4, as do flies overexpressing the snoRNA (G5) (b2). F4 mutant flies re-expressing the snoRNA specifically in enterocytes (Myo,F4/F4; UAS-snoRNA) (c2) also have fewer lesions than those not expressing it (Myo,F4/F4) (c1). In (d), quantification of lesions in young flies (4 days old) and old flies (40 days old) for these various genotypes. All these results show that the expression of the snoRNA protects against neurodegenerative lesions in old flies (0, +, ++, +++=degree of severity of lesions based on their number and area).
Figure 12:
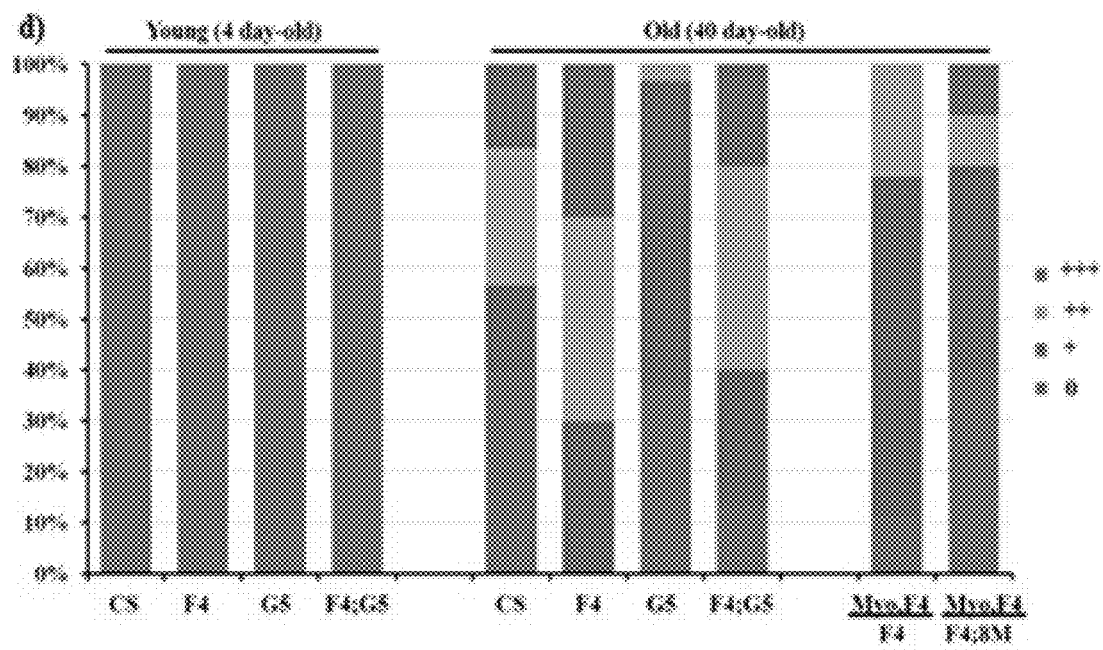

Since F4 flies have a very short lifespan, while flies overexpressing the snoRNA (G5) live longer, the old flies (40 days old) were studied in order to check for the presence of any neurodegenerative lesions (more or fewer holes of larger or smaller size present in the brain). Overall, in the control flies (Canton-S), around 60% of flies present lesions (but note that 50% of the CS flies are already dead at 40 days) (FIG. 12) (for further detail, see FIG. 12d for a semi-quantitative analysis). In F4 mutants, all the flies (100%) have lesions, and they are generally more severe than those of controls (size and number of holes), while F4;G5 flies have significantly fewer holes (only about 10% of the flies), these holes also being of smaller size. Finally, in the G5 flies, around the same percentage of flies as the CS controls present lesions (around 40%), but these lesions are clearly less severe (FIG. 12d). In summary, the genomic transgene (F4;G5) partially rescues the neurodegeneration phenotype, while overexpression of the snoRNA (G5) protects against neurodegeneration.

10) Role of the snoRNA in Protection of Sensorimotor Parameters.

Figure 13A:
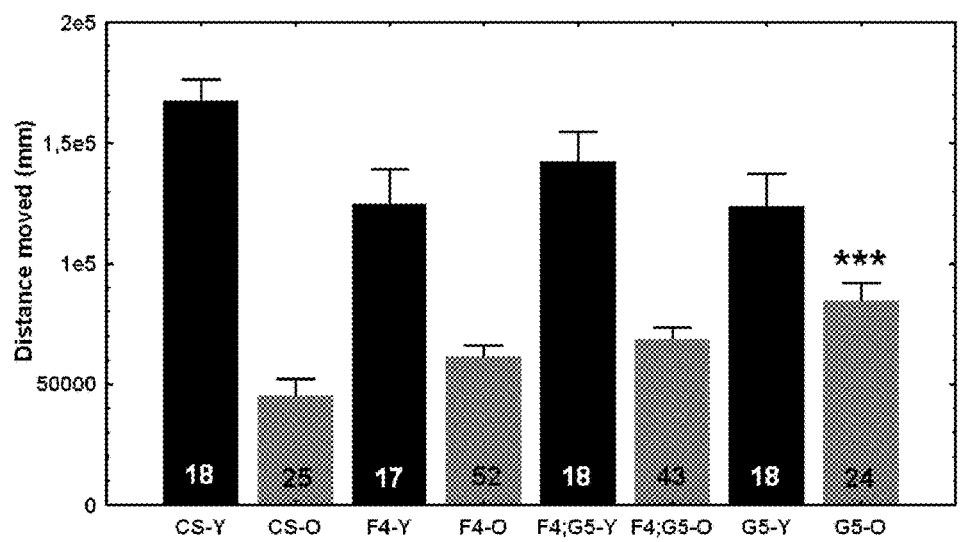
FIGS. 13A-13B: A sensorimotor parameter (locomotor activity) quantified by video tracking, represented here by the distance travelled during 7 hours of recording. Forty-day-old flies are compared to young 4-day-old flies.
Figure 13B:
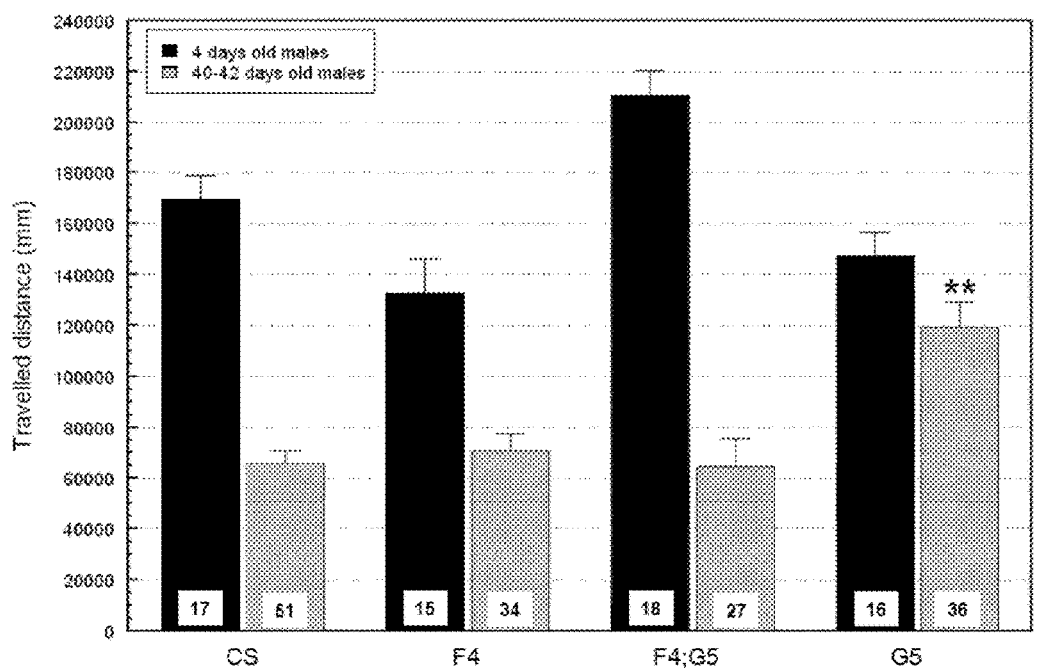

Similarly, in order to ascertain whether the neuroprotection provided by the snoRNA has effects on physiological parameters such as sensorimotor parameters, the locomotor activity of flies older than 40 days was quantified (by video-tracking) (Martin, 2004) and compared to those of young flies, aged 4 days (FIG. 13). Firstly, an enormous difference between the 4-day-old flies and the 40-day-old ones is observed; the 40-day-old flies travel a third of the distance of that travelled by the 4-day-old flies. However, in the elderly 40-day-old flies, the flies that overexpress the snoRNA (G5) walk more than the control flies (Canton-S), F4 mutants, and those expressing the snoRNA in the genetic mutant background (F4;G5). This effect is more marked in males than in females. In summary, in elderly 40-day old flies, we see that the flies overexpressing the snoRNA have better sensorimotor performance than control flies. These results demonstrate the protective nature of the snoRNA relative to the harmful effects associated with mechanisms of aging.

11) Testing the Function of the snoRNA in the Ovaries: Role in Fertility (Reproduction).

Figure 14A:
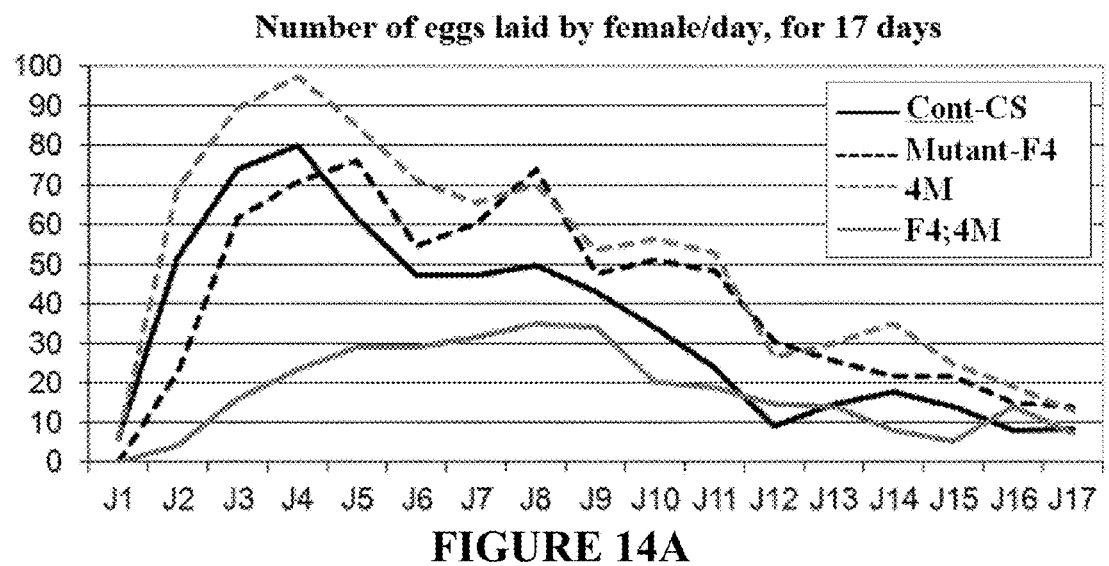
FIGS. 14A-14B: Fly fertility (number of eggs laid (FIG. 14A) per female/day and (FIG. 14B) per female in 17 days). In all, the F4 mutants lay a few more eggs than the controls (CS), but with a slight delay. The expression of the transgene (snoRNA) in the F4 mutant (F4;G4—also called F4;4M) reduces fertility. Overexpression of the transgene (G4—also called 4M) increases fertility (number of eggs laid).
Figure 14B:
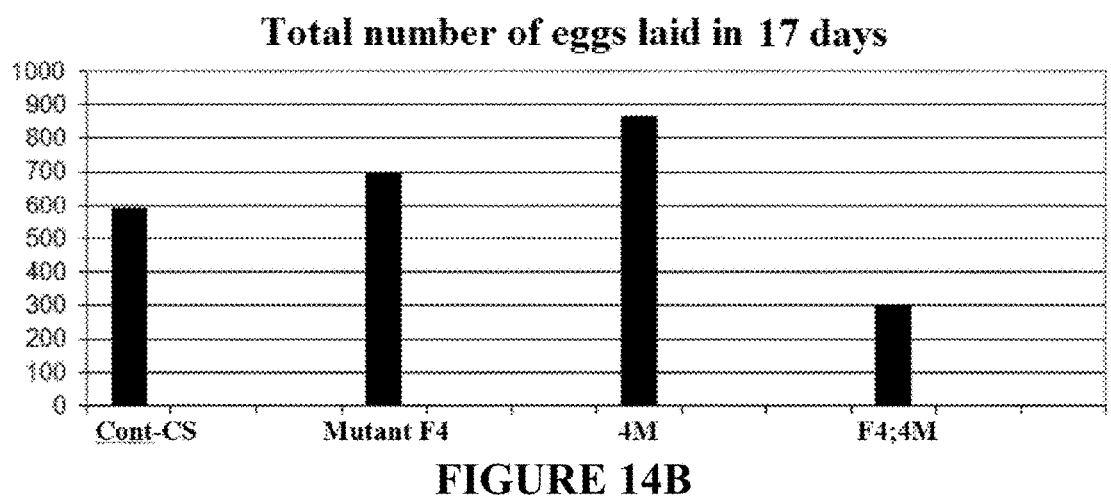

In females, the snoRNA is also expressed in the ovaries and more precisely in nurse cells (FIGS. 5C-D). The inventor has also shown that mutant flies (F4) also have fertility changes (reproducer phenotype). The F4 mutants lay a few more eggs than the control flies (CS) (FIG. 14). The flies bearing the snoRNA in the mutant genetic background (F4;G4) lay many fewer eggs (reduced fertility) while flies overexpressing the snoRNA (G4) lay many more eggs than the control flies (FIG. 14). These results undeniably demonstrate the important effect exerted by the snoRNA in the ovaries and its influence on fertility in females.

12) Treatment with the snoRNA (Administration by Oral Route or Injection).

The snoRNA can be administered either orally (per os) or by injection. Other administration routes, such as inhalation and local/cutaneous application can also be used depending on the type of vector used.

As the experiments conducted as part of the invention show, oral administration of the snoRNA is possible given its stability and in vitro resistance as well as its ability to act locally on the cells of the intestinal wall (enteroblasts, enterocytes, ISCs). As explained previously, the administration of the snoRNA of interest is therefore able to permit expression that would otherwise be absent (or, in other words, to rescue an existing mutation) or, if necessary, permit overexpression, in order to protect the intestinal wall from damage while maintaining a better hormonal and metabolic equilibrium.

13) Cancer Treatment.

Figure 15A:
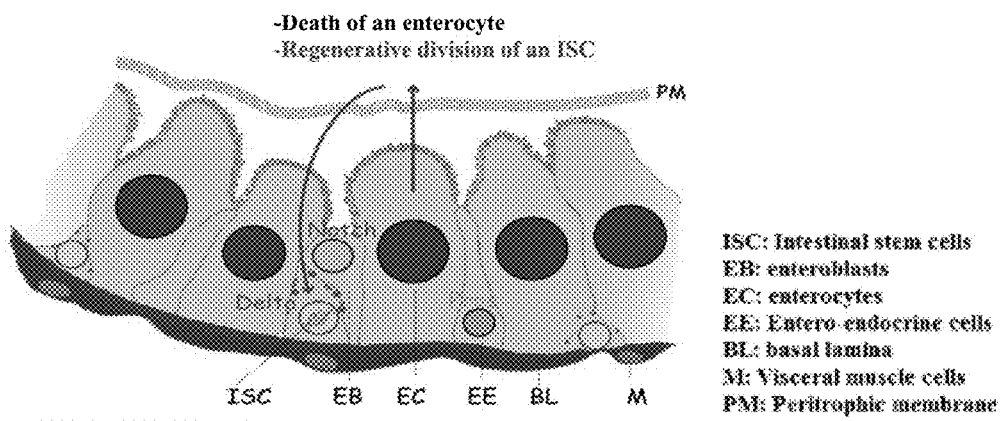
FIGS. 15A-15B: Diagram of the intestinal epithelium (Extract from Jiang and Edgar, *Exp. Cell. Res.*, 2011).
Figure 15B:
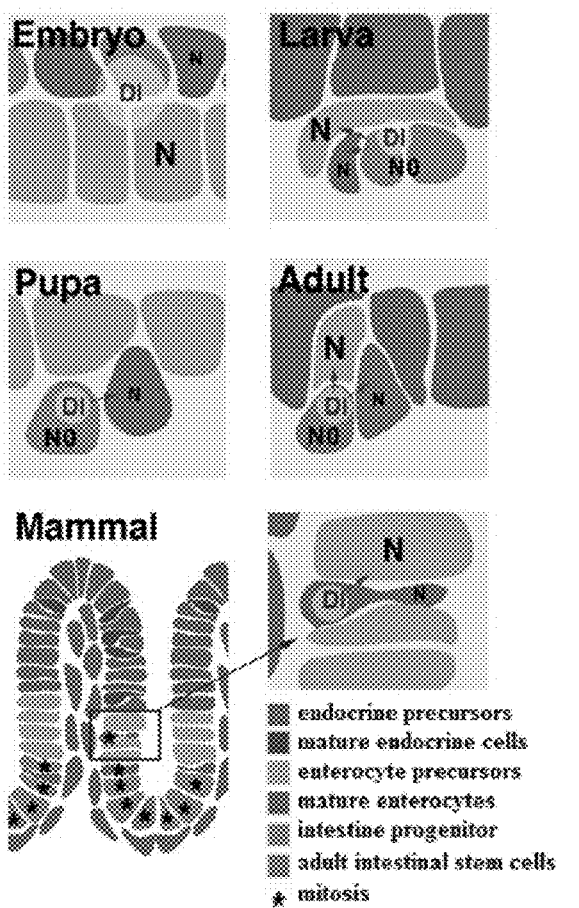
Figure 16:
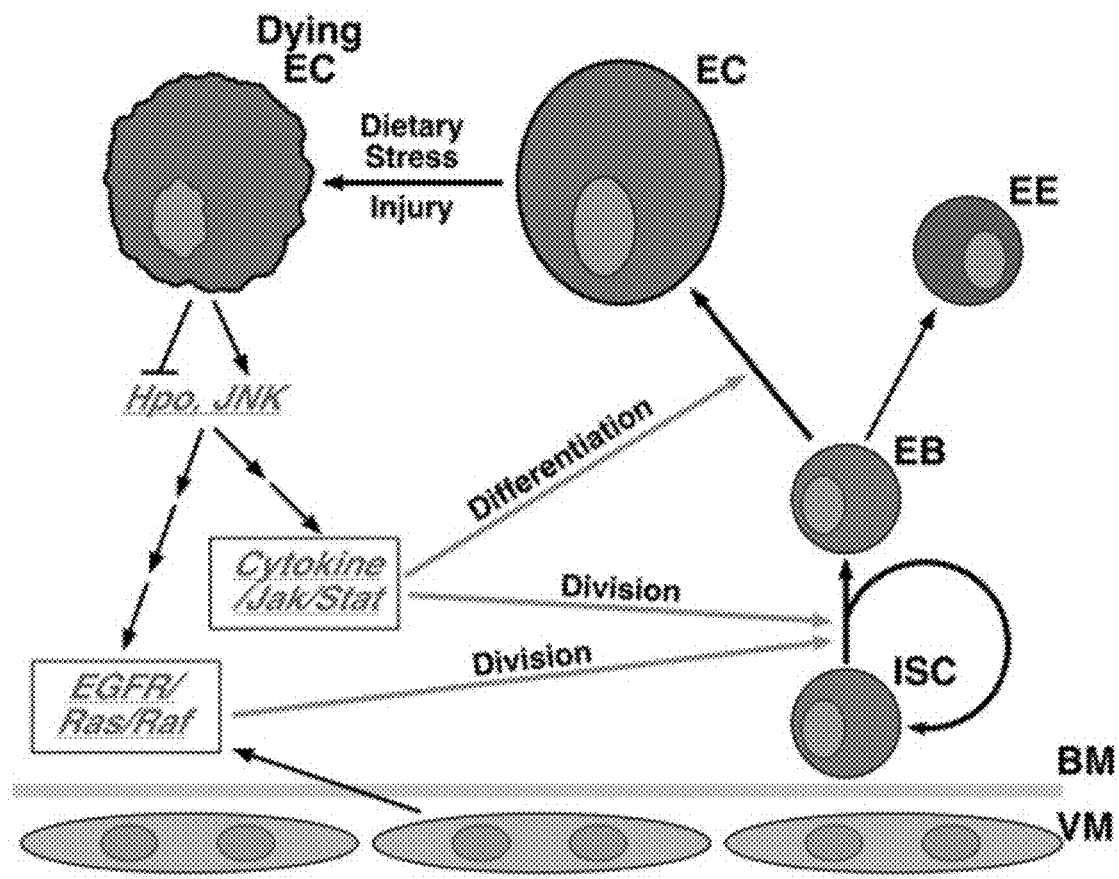
FIG. 16: Retro-control mechanism regulating intestine homeostasis and regeneration (midgut) in the *Drosophila* (Extract from Jiang and Edgar, Exp. Cell. Res., 2011) (same abbreviation as FIG. 15).
Figure 17:
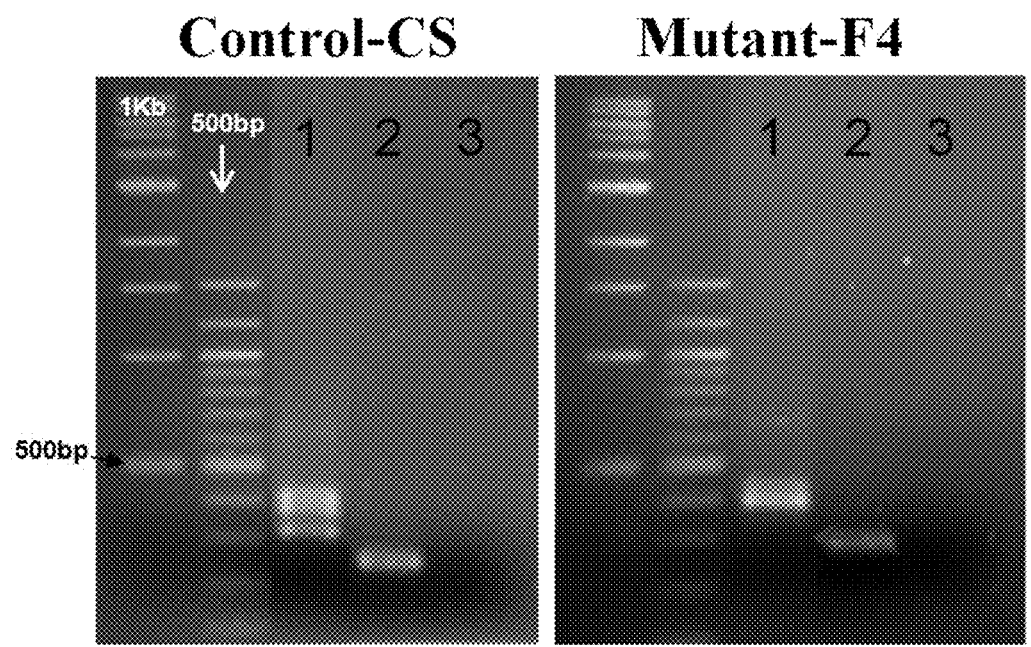
FIG. 17: The youth snoRNA is involved in the alternative splicing of gene CG9339 (skywalker). Comparative RT-PCR was done in some potential target genes in order to see if, in the F4 mutant, some of these genes were not spliced correctly relative to wildtype flies (Control-CS). Among others, 4 transcripts of 345-400-432-462 bp of gene CG9339 (skywalker) were analyzed. The rp49 gene (300-bp fragment) is used as an internal control, as well as a control with RNA (with no RT beforehand) in order to demonstrate that the RNA used is not contaminated by traces of DNA. Note the absence of the small 345-bp transcription of gene CG9339 (skywalker) in the F4 mutant (arrow).
Figure 19A:
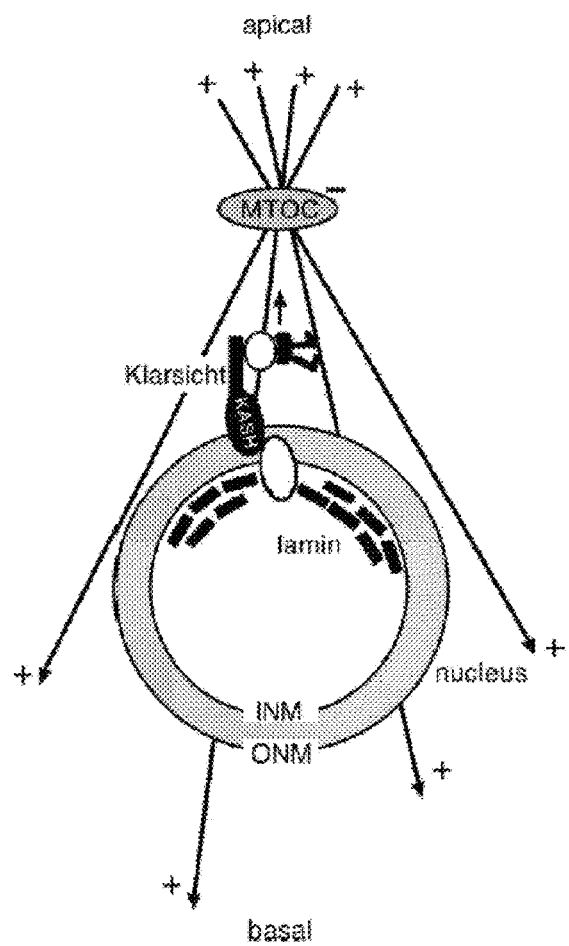
FIGS. 19A-19B: Model describing the role of klarsicht.
Figure 19B:
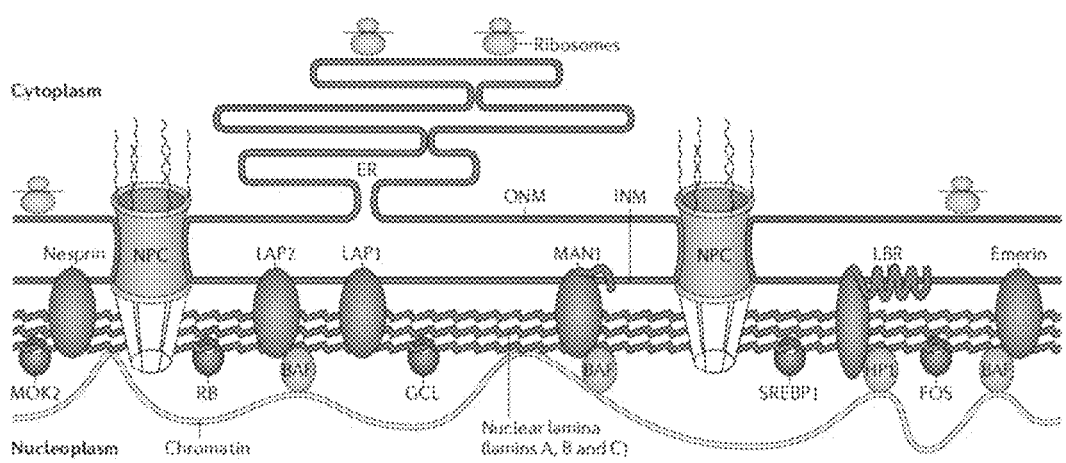

In both mammals and *Drosophila*, it was shown that the delta/notch genes regulate the differentiation of intestine (gut) progenitor cells, while the Wnt signalling pathway participates in maintenance and proliferation of ISCs. Likewise, the cytokine signalling pathways (Upd/Jak/Stat) and the EGFR (Epidermal Growth Factor Receptor) pathway regulate the proliferation of ISCs (FIGS. 15-16) (Jiang and Edgar, 2011; Takashima et al., 2011).

The inventor's experiments show that the snoRNA of interest according to the invention is able to regulate certain genes, such as notch, delta, JNK, EGFR, etc. (FIG. 15), whose deregulation could lead to hyperproliferation of the intestinal epithelium and therefore to cancer (Jiang and Edgar, 2011; Takashima et al., 2011). The snoRNA of interest of the invention is particularly able to prevent or treat cancer through its ability to regulate the expression of EGFR, the EGFR signaling pathway in the regulation of proliferation of ISCs in the intestine of *Drosophila* and mammals being, in fact, particularly well conserved (FIG. 16) [several therapies are currently under clinical trial for the treatment of colon cancer, including two anti-EGFR monoclonal antibodies (cetuximab and panitumumab) (Amado et al., 2008; Di Nicolantonio et al., 2008)].

14) Involvement of the snoRNA of Interest ("Youth") in Hutchinson-Gilford Progeria Syndrome (HGPS), Also Known as Progeria, which Consists of Early and Accelerated Aging in Humans.

The inventor has demonstrated that the youth snoRNA regulates splicing (quantity of spliced RNA) of the klarsicht gene (FIG. 18A). It has been shown that this gene interacts with the lamina (Patterson et al., 2004), a protein located in the inner membrane of the nucleus and involved in progeria (disease causing early and accelerated aging in humans) (FIG. 18B). Progeria is a rare disease affecting 1 in 8 million individuals (Scaffidi and Misteli, 2006; Broers et al., 2006; Cohen et al., 2001; Cau et al., 2014; Coutinho et al., 2009).

The youth snoRNA provides, through its phenotype (involvement in longevity) and its involvement in the regulation of the klarsicht gene, a novel prospect for treating laminopathies such as Hutchinson-Gilford progeria syndrome, mandibuloacral dysplasia (MAD), Emery-Dreifuss muscular dystrophy, atypical Werner syndrome, restrictive dermatopathy, lethal fetal akinesia, and LIRLLC (Generalized lipoatrophy, insulin-resistant diabetes, leukomelanodermic papules, liver steatosis, and hypertrophic cardiomyopathy) (Hutchison, 2002; Broers et al, 2006), in particular Hutchinson-Gilford progeria syndrome (progeria).

15) Involvement of the snoRNA of Interest ("Youth") in the Regulation of Fatty Acid 2-Hydroylase (fa2h) Gene Splicing, and Consequently with the Various Forms of Neurodegeneration Associated with this Gene.

The inventor has demonstrated that the youth snoRNA regulates splicing (quantity of RNA spliced) of the gene CG30502 coding for fatty acid 2-hydroxylase (fa2h) (FIG. 18B). This gene is involved in the process of fatty acid biosynthesis and more particularly in the metabolic processes of complex lipids such as sphingolipids and ceramides (Carvalho et al., 2010). In humans, fa2h has been associated with various forms of neurodegeneration (demyelinization), such as those associated with iron accumulation in the brain, certain leukodystrophies, and finally hereditary spastic paraplegia (SPG35) (Kruer et al., 2010; Pierson et al., 2012; Schneider and Bhatia, 2010). Due to its phenotype (involvement in longevity and/or fat body hypertrophy observed in the F4 mutant) and its involvement in the regulation of the fa2h gene, the youth snoRNA offers a novel prospect for treatment of the neurodegenerative diseases mentioned above.

16) Metabolic and Neuro-Endocrinal Relationship Between the Intestine and the Brain (Brain-Gut Axis).

Figure 21:
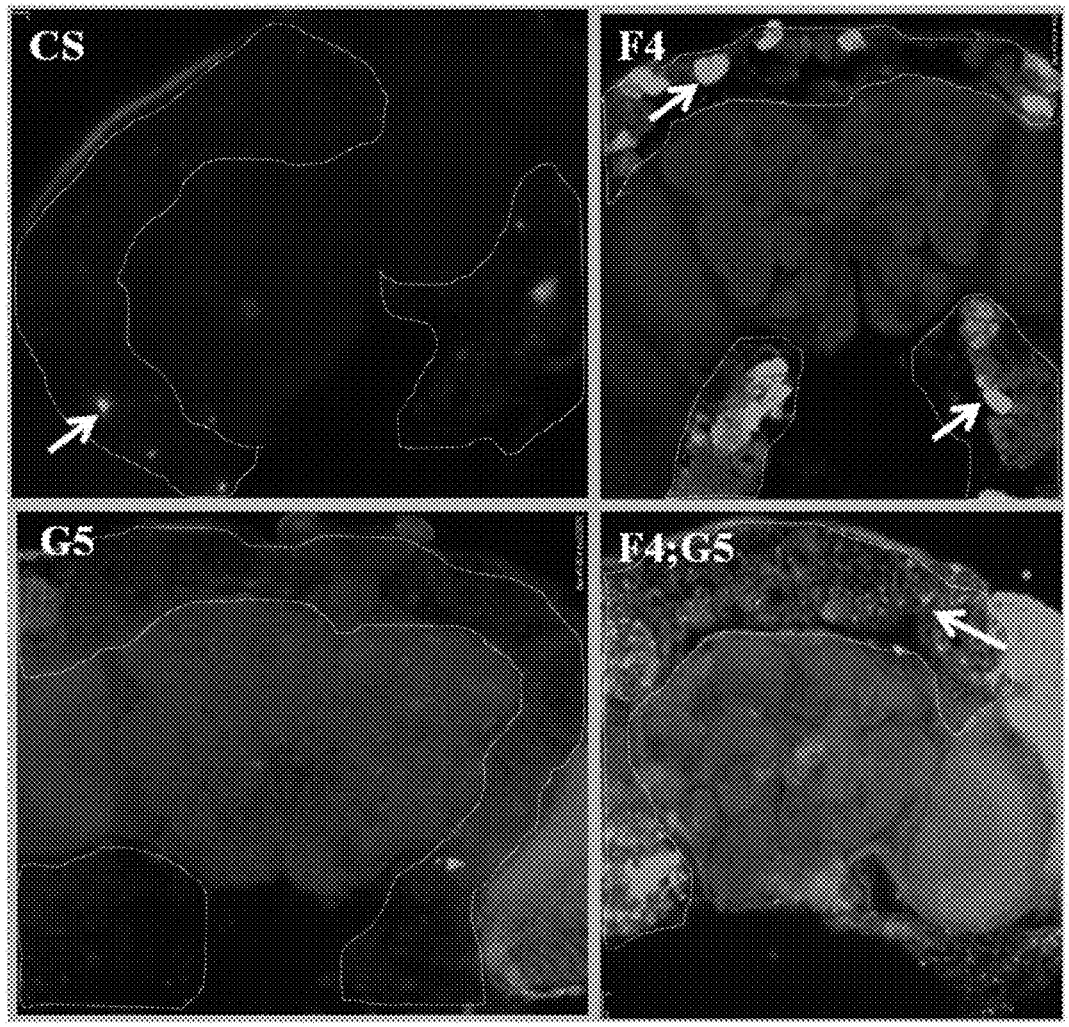
FIG. 21: Flies mutated for the youth snoRNA (F4 mutant) show fat body hypertrophy. Significant alterations thereof are observed in 40-day old elderly flies compared to their respective controls, also 40 days old. These lesions are shown by activated anti-caspase-3 antibody labeling, which labels cells undergoing apoptosis. "CS" control flies: The fat body, surrounded by a white dotted line, is fairly homogeneous and smooth. F4 mutant flies: note large cell aggregates (white arrow). In flies bearing the snoRNA transgene (G5), the fat body, without aggregate, resembles the fat body of the "CS" control. Flies with the G5 transgene in the F4 mutant genetic background (F4;G5) only show a few aggregates, and these aggregates are smaller, which indicates that the transgene partially rescues the fat body lesions due to the mutation. These results strongly suggest a disruption in the metabolism of carbohydrates and fats.

As mentioned previously, snoRNA mutants (F4) present fat body hypertrophy, visible both at the abdomen and around the brain in the head capsule (FIG. 21). Furthermore, triglyceride quantification confirmed this hypertrophy (hence the "obese" qualifier of the flies). This phenotype suggests a metabolic and/or neuroendocrine relationship between the expression of the snoRNA in the intestine, neurodegenerative lesions and increased lifespan. More specifically, this metabolic disruption suggests an involvement of the insulin signalling pathway, this pathway being described many times as involved in *Drosophila* longevity (Tatar et al., 2001; Bai et al., 2012; Partridge et al., 2011; Fontana et al., 2010). Immunohistochemical markers directed against activated anti-caspase-3 have shown, in adult *Drosophila*, that the fat located around the perimeter of the brain is greatly disrupted (i.e., hypertrophied) in F4 mutants, while it is protected by overexpression of the snoRNA (transgene G5) as well as in the rescue (restoration of expression) (F4; G5) (FIG. 21). These results demonstrate that the snoRNA protects the organism that expresses it from changes in the fat body, and therefore, by extension, from obesity. Furthermore, genetic interaction experiments (double mutants) involving insulin receptor (InR) mutations and the F4 mutant show that mutation of the snoRNA can at least partially rescue the phenotype of the insulin receptor mutation (see FIG. 21 and its caption). These results show the existence of links (whether direct or indirect) between the insulin signalling pathway, the snoRNA and longevity. The preceding results show that mutation and/or deregulation of the snoRNA disrupts carbohydrate and lipid metabolism.

The youth snoRNA therefore offers a novel prospect for treating both diabetes and obesity.

17) Expression of the snoRNA of Interest ("Youth") in Humans and Mice.

Figure 20:
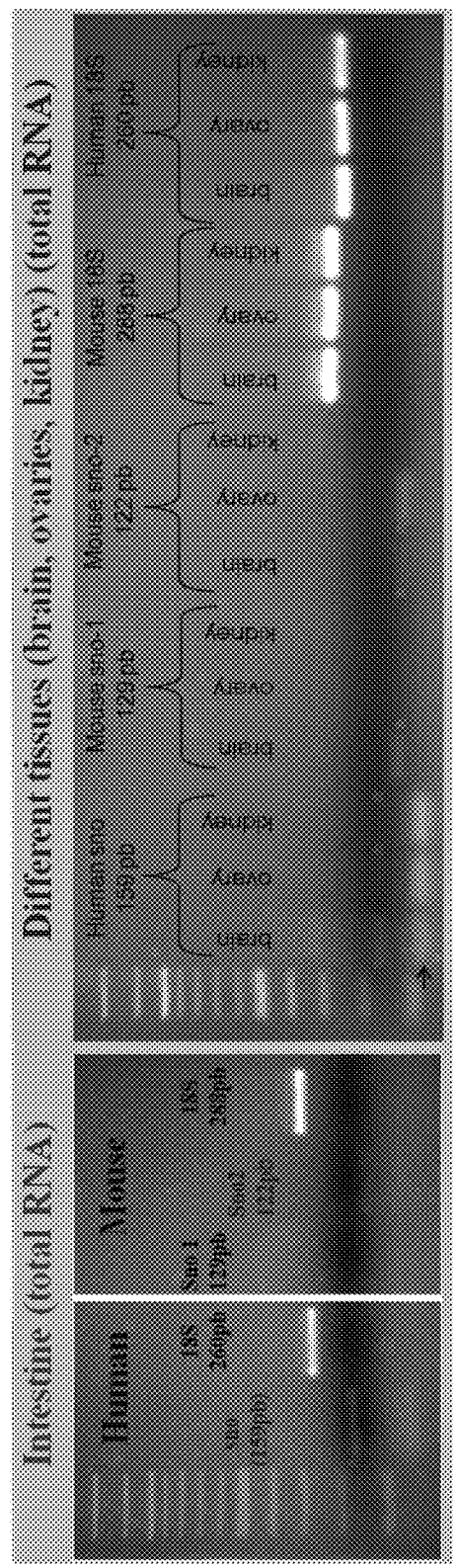
FIG. 20: Orthologous mammal sequences of the youth snoRNA are expressed in mice and humans (detection by RT-PCR of mice and human homologs). The expression of these snoRNAs indicates that they are very likely to be functional. In humans, the 159-bp snoRNA (SEQ ID NO: 2) is expressed in the intestine and brain and slightly in the ovaries and kidneys (marked with a red asterisk for more precision). In mice, the 129-bp snoRNA-1 (SEQ ID NO: 3) is expressed only in the brain. In contrast, the 122-bp snoRNA-2 (SEQ ID NO: 4) is expressed in the intestine, brain and ovaries, but not in the kidneys.

By an RT-PCR approach, the inventor has demonstrated the existence of homologous sequences, more precisely orthologous sequences, to the youth snoRNA (first identified in *Drosophila*) concretely expressed in mammals (FIG. 20). In humans, the 159-bp snoRNA (SEQ ID NO: 2) is expressed in the intestine and brain and slightly in the ovaries and kidneys. In mice, the 129-bp snoRNA-1 (SEQ ID NO: 3) is expressed only in the brain and the 122-bp snoRNA-2 (SEQ ID NO: 4) is expressed in the intestine, brain and ovaries, but not in the kidneys. These data support the expression, very likely to be functional, of these snoRNAs in both humans and mice.

REFERENCES

Amado R G, Wolf M, Peeters M, Van Cutsem E, Siena S, Freeman D J, Juan T, Sikorski R, Suggs S, Radinsky R, Patterson S D, Chang D D (2008). Wild-type KRAS is required for panitumumab efficacy in patients with metastatic colorectal cancer. *J Clin Oncol*, 26, 1626-1634.

Bai H, Kang P, Tatar M. (2012). *Drosophila* insulin-like peptide-6 (dilp6) expression from fat body extends lifespan and represses secretion of *Drosophila* insulin-like peptide-2 from the brain. *Aging Cell.*, 11, 978-985.

Brand A H, Perrimon N (1993) Targeted gene expression as a means of altering cell fates and generating dominant phenotypes. *Development* 118, 401-415.

Broers J L, Ramaekers F C, Bonne G, Yaou R B, Hutchison C J (2006). Nuclear lamins: laminopathies and their role in premature ageing. *Physiol Rev.*, 86, 967-1008.

Carvalho M, Schwudke D, Sampaio J L, Palm W, Riezman I, Dey G, Gupta G D, Mayor S, Riezman H, Shevchenko A, Kurzchalia T V, Eaton S. (2010) Survival strategies of a sterol auxotroph. *Development*, 137, 3675-3685.

Cau P, Navarro C, Harhouri K, Roll P, Sigaudy S, Kaspi E, Perrin S, De Sandre-Giovannoli A, Lévy N. (2014). Nuclear matrix, nuclear envelope and premature aging syndromes in a translational research perspective. *Semin Cell Dev Biol.*, 28, S1084-9521(14)00058-5.

Cohen M, Lee K K, Wilson K L, Gruenbaum Y. (2001). Transcriptional repression, apoptosis, human disease and the functional evolution of the nuclear lamina. *Trends Biochem Sci.*, 26, 41-47.

Coutinho H D, Falcâlo-Silva V S, Gonçalves G F, da Nóbrega R B (2009). Molecular ageing in progeroid syndromes: Hutchinson-Gilford progeria syndrome as a model. *Immun Ageing*, 20, 6:4.

Dick, K. J., Al-Mjeni, R., Baskir, W., Koul, R., Simpson, M. A., Patton, M. A., Raeburn, S., Crosby, A. H. (2008). A novel locus for an autosomal recessive hereditary spastic paraplegia (SPG35) maps to 16q21-q23. *Neurology* 71: 248-252.

Dick, K. J., Eckhardt, M., Paisan-Ruiz, C., Alshehhi, A. A., Proukakis, C., Sibtain, N. A., Maier, H., Sharifi, R., Patton, M. A., Bashir, W., Koul, R., Raeburn, S., Gieselmann, V., Houlden, H., Crosby, A. H. (2010). Mutation of FA2H underlies a complicated form of hereditary spastic paraplegia (SPG35). *Hum. Mutat.* 31: E1251-1260.

Di Nicolantonio F, *Martini* M, Molinari F, Sartore-Bianchi A, Arena S, Saletti P, De Dosso S, Mazzucchelli L, Frattini M, Siena S, Bardelli A (2008). Wild-type BRAF is required for response to panitumumab or cetuximab in metastatic colorectal cancer. *J Clin Oncol*, 26, 5705-5712.

Elliott D A, Brand A H. (2008) The GAL4 system: a versatile system for the expression of genes. *Methods Mol Biol*, 420, 79-95.

Fontana L, Partridge L, Longo V L (2010). Extending healthy life span—from yeast to humans. *Science*, 328, 321-326.

Huang Z P, Zhou H, He H L, Chen C L, Liang D, Qu L H. (2005) Genome-wide analyses of two families of snoRNA genes from *Drosophila melanogaster*, demonstrating the extensive utilization of introns for coding of snoRNAs. *RNA*, 11, 1303-1316.

Hutchison C J. (2002). Lamins: building blocks or regulators of gene expression? *Nat Rev Mol Cell Biol.*, 3, 848-858.

Jiang H, Edgar B A (2011). Intestinal stem cells in the adult *Drosophila* midgut. *Exp Cell Res.* 317, 2780-2788.

Kruer M C, Paisán-Ruiz C, Boddaert N, Yoon M Y, Hama H, Gregory A, Malandrini A, Woltjer R L, Munnich A, Gobin S, Polster B J, Palmeri S, Edvardson S, Hardy J, Houlden H, Hayflick S J. (2010). Defective FA2H leads to a novel form of neurodegeneration with brain iron accumulation (NBIA). *Ann Neurol.*, 68, 611-618.

Martin, J R, Faure, P, Ernst, R (2002). The Power Law Distribution for Walking-Time Intervals Correlates with the Ellipsoid Body in *Drosophila. J. Neurogenetics*, 15, 1-15.

Martin, J R (2004). A portrait of locomotor behaviour in *Drosophila* determined by a video-tracking paradigm. *Behav. Process.*, 67, 207-219.

Partridge L, Alic N, Bjedov I, Piper M D (2011). Ageing in *Drosophila*: the role of the insulin/Igf and TOR signalling network. *Exp Gerontol.*, 46, 376-381.

Patterson K, Molofsky A B, Robinson C, Acosta S, Cater C, Fischer J A. (2004) The functions of Klarsicht and nuclear lamin in developmentally regulated nuclear migrations of photoreceptor cells in the *Drosophila* eye. *Mol Biol Cell.*, 15, 600-610.

Pierson T M, Simeonov D R, Sincan M, Adams D A, Markello T, Golas G, Fuentes-Fajardo K, Hansen N F, Cherukuri P F, Cruz P, Mullikin J C, Blackstone C, Tifft C, Boerkoel C F, Gahl W A. (2012) Exome sequencing and SNP analysis detect novel compound heterozygosity in fatty acid hydroxylase-associated neurodegeneration. *Eur J Hum Genet.*, 20, 476-479.

Rzezniczak T Z, Douglas L A, Watterson J H, Merritt T J. (2011) Paraquat administration in *Drosophila* for use in metabolic studies of oxidative stress. *Analytical Biochem.*, 419, 345-7.

Scaffidi P, Misteli T. (2006) Lamin A-dependent nuclear defects in human aging. *Science*, 312, 1059-1063.

Schneider S A, Bhatia K P. (2010) Three faces of the same gene: FA2H links neurodegeneration with brain iron accumulation, leukodystrophies, and hereditary spastic paraplegias. *Ann Neurol.*, 68, 575-577.

Takashima S, Adams K L, Ortiz P A, Ying C T, Moridzadeh R, Younossi-Hartenstein A, Hartenstein V (2011). Development of the *Drosophila* entero-endocrine lineage and its specification by the Notch signaling pathway. *Dev Biol*, 353, 161-172.

Tatar M, Kopelman A, Epstein D, Tu M P, Yin C M, Garofalo R S (2001). A Mutant *Drosophila* Insulin Receptor Homolog That Extends Life-Span and Impairs Neuroendocrine Function. *Science*, 292, 107.

Uytterhoeven V, Kuenen S, Kasprowicz J, Miskiewicz K, Verstreken P (2011). Loss of skywalker reveals synaptic endosomes as sorting stations for synaptic vesicle proteins. *Cell*, 145, 117-132.

The invention claimed is:

1. An isolated or synthetic RNA sequence comprising SEQ ID NO: 1, or an orthologous sequence, said isolated or synthetic RNA sequence being chemically modified, said chemical modification comprising amination, halogenation, modification of a sugar group on said isolated or synthetic RNA sequence, a nucleotide comprising a heterocyclic base incapable of creating hydrogen bonds with heterocyclic DNA or RNA bases, or a modification of an internucleoside link selected from a phosphorothioate, methylphosphonate, phosphotriester, phosphorodithioate and phosphoselenate bond.

2. The RNA sequence according to claim 1, characterized in that said orthologous sequence is of human origin and consists of SEQ ID NO: 2 or is of mouse origin and consists of a sequence chosen from SEQ ID NO: 3 and SEQ ID NO: 4.

3. The RNA sequence according to claim 1, characterized in that said sequence is a small nucleolar RNA (snoRNA).

4. The RNA sequence according to claim 1, said sequence splicing a *Drosophila melanogaster* gene selected from the group consisting of Ir56d, buttonhead, klarsicht, CG3262, CG30502 (fa2h), CG11125, CG9339 and CG40006.

5. A method of extending the lifespan of a subject, increasing stress resistance, or fighting the harmful effects of aging in a subject comprising the administration of an isolated or synthetic RNA sequence comprising SEQ ID NO: 1 or an orthologous sequence thereof to a subject, said RNA sequence being, optionally, chemically modified.

6. A method of treating a disease in a subject comprising the administration of an isolated or synthetic RNA sequence comprising SEQ ID NO: 1 or an orthologous sequence thereof to a subject, said RNA sequence being, optionally, chemically modified.

7. The method of claim 6, wherein said disease is a degenerative disease; a neurodegenerative disease; a laminopathy; diabetes; obesity; or cancer.

8. A method of treating infertility or stimulating fertility in a subject comprising the administration of an isolated or synthetic RNA sequence comprising SEQ ID NO: 1 or an orthologous sequence thereof to a subject, said RNA sequence being, optionally, chemically modified.

9. A nucleic acid construct comprising a DNA sequence encoding the RNA sequence of SEQ ID NO: 1 operably linked to a heterologous promoter.

10. A vector comprising a DNA sequence encoding an RNA sequence comprising SEQ ID NO: 1 or an orthologous sequence thereof.

11. A cell transformed with a vector encoding an RNA sequence comprising SEQ ID NO: 1 or an orthologous sequence thereof.

12. A composition comprising a RNA sequence according to claim 1 and a dietarily- or pharmaceutically-acceptable support.

* * * * *

SEQUENCE LISTING

<160> NUMBER OF SEQ ID NOS: 43

<210> SEQ ID NO 1
<211> LENGTH: 148
<212> TYPE: RNA
<213> ORGANISM: Drosophila melanogaster

<400> SEQUENCE: 1

| aaagcguuag auauuaaacu gugguugaau ucacaaaaua ggccacaguu augcaauaaa | 60 |
| cgcuagaaaa aaaacgguag uauuuaauaa cguuugacu aacaucugcg gauaagaagc | 120 |
| uuugcguuuu gagguacuaa ccacagua | 148 |

<210> SEQ ID NO 2
<211> LENGTH: 159
<212> TYPE: RNA
<213> ORGANISM: Homo sapiens

<400> SEQUENCE: 2

| guaaguguag ccuagaaauu ggggcuggau uugaaaauua gccccaauuc ugcaauuuuc | 60 |
| accgcaauaa aagcuucucc aguuauacau ggugauggu cuugaugggc uauguggac | 120 |
| agaggagggu gcuagguugg gguggacggg gccacagcu | 159 |

<210> SEQ ID NO 3
<211> LENGTH: 129
<212> TYPE: RNA
<213> ORGANISM: Mus musculus

<400> SEQUENCE: 3

| aaaggggung aagaauggua uggauucaga augaacuauc agagaaacuc cagagccagc | 60 |
| aggaaacauu auagagccuu ugcuacaaug uccuguuucu uucuuggcuu uuaguucugu | 120 |
| uccacagau | 129 |

<210> SEQ ID NO 4
<211> LENGTH: 122
<212> TYPE: RNA
<213> ORGANISM: Mus musculus

<400> SEQUENCE: 4

| gaaagcauuu aauauuuacc aauaguuuau uccgagcuag gguaaagcag ucagugcuag | 60 |
| aaaaaugaga aaacacaaua cauaagaccu cucaagggga gaugcuguua cuguauauac | 120 |
| ug | 122 |

<210> SEQ ID NO 5
<211> LENGTH: 147
<212> TYPE: DNA
<213> ORGANISM: Drosophila melanogaster

<400> SEQUENCE: 5

| aaagcgttag atattaaact gtggttgaat tcacaaaata ggccacagtt atgcaataaa | 60 |
| cgctagaaaa aaaacggtagt atttaataac gtgttgacta acatctgcgg ataagaagct | 120 |
| ttgcgttttg aggtactaac cacagta | 147 |

<210> SEQ ID NO 6
<211> LENGTH: 159
<212> TYPE: DNA
<213> ORGANISM: Homo sapiens

<400> SEQUENCE: 6

```
gtaagtgtag cctagaaatt ggggctggat ttgaaaatta gccccaattc tgcaattttc      60
accgcaataa aagcttctcc agttatacat ggtgattggt cttgatgggc tattgtggac     120
agaggagggt gctaggttgg ggtggacggg gccacagct                            159

<210> SEQ ID NO 7
<211> LENGTH: 129
<212> TYPE: DNA
<213> ORGANISM: Mus musculus

<400> SEQUENCE: 7 aaagggttg aagaatggta tggattcaga atgaactatc agagaaactc cagagccagc      60
aggaaacatt atagagcctt tgctacaatg tcctgtttct ttcttggctt ttagttctgt    120
tccacagat                                                            129

<210> SEQ ID NO 8
<211> LENGTH: 122
<212> TYPE: DNA
<213> ORGANISM: Mus musculus

<400> SEQUENCE: 8
gaaagcattt aatatttacc aatagtttat tccgagctag ggtaaagcag tcagtgctag     60
aaaaatgaga aaacacaata cataagacct ctcaagggga gatgctgtta ctgtatatac    120
tg                                                                   122

<210> SEQ ID NO 9
<211> LENGTH: 149
<212> TYPE: RNA
<213> ORGANISM: Drosophila simulans

<400> SEQUENCE: 9
aaagcguuag guauaaaccu gugguugaau ucacaaaaua ggccacaguu augcaauaaa     60
cgcuagaaaa aaaacgguag uauuuaauaa cguguugacu aacaucugcg gauaaaacag    120
cuuugcguuu ugagguacua accacagua                                      149

<210> SEQ ID NO 10
<211> LENGTH: 149
<212> TYPE: DNA
<213> ORGANISM: Drosophila simulans

<400> SEQUENCE: 10
aaagcgttag gtataaacct gtggttgaat tcacaaaata ggccacagtt atgcaataaa     60
cgctagaaaa aaaacggtag tatttaataa cgtgttgact aacatctgcg gataaaacag    120
ctttgcgttt tgaggtacta accacagta                                      149

<210> SEQ ID NO 11
<211> LENGTH: 149
<212> TYPE: RNA
<213> ORGANISM: Drosophila sechellia

<400> SEQUENCE: 11
aaagcguuag guauuaaccu gugguuuaau ucacaaaaua ggccacaguu augcaauaaa     60
cgcuagaaaa aaaacgguag uauuuaauaa cguguugacu aacaucugcg gauaaaauag    120
cuuugcguuu ugagguacua accacagua                                      149

<210> SEQ ID NO 12
```

<210> SEQ ID NO 12
<211> LENGTH: 149
<212> TYPE: DNA
<213> ORGANISM: Drosophila sechellia

<400> SEQUENCE: 12

```
aaagcgttag gtattaacct gtggtttaat tcacaaaata ggccacagtt atgcaataaa      60
cgctagaaaa aaaacggtag tatttaataa cgtgttgact aacatctgcg gataaaatag     120
ctttgcgttt tgaggtacta accacagta                                       149
```

<210> SEQ ID NO 13
<211> LENGTH: 147
<212> TYPE: RNA
<213> ORGANISM: Drosophila yakuba

<400> SEQUENCE: 13

```
caagcguugu auaauauuaa acuguggaaa cuucacaaau aggccacagu uaugcaagaa      60
acgcuagaaa aacuugguag uauuuaauaa cgugcugacu aacgucugcg gauaaaagcu     120
uugcguuuug agguacuaac cacauua                                         147
```

<210> SEQ ID NO 14
<211> LENGTH: 147
<212> TYPE: DNA
<213> ORGANISM: Drosophila yakuba

<400> SEQUENCE: 14

```
caagcgttgt ataatattaa actgtggaaa cttcacaaat aggccacagt tatgcaagaa      60
acgctagaaa aacttggtag tatttaataa cgtgctgact aacgtctgcg gataaaagct     120
ttgcgttttg aggtactaac cacatta                                         147
```

<210> SEQ ID NO 15
<211> LENGTH: 148
<212> TYPE: RNA
<213> ORGANISM: Drosophila erecta

<400> SEQUENCE: 15

```
caugcguuga auaauauuaa acuguggacg aauucccaaa uaagccacag uuaugcaaga      60
aacgcuagaa aaauagguua guauuuaaua acgugcugac uaacaucugc ggauaagagc     120
uuugcguuuu gagguacuaa ccacaaua                                        148
```

<210> SEQ ID NO 16
<211> LENGTH: 148
<212> TYPE: DNA
<213> ORGANISM: Drosophila erecta

<400> SEQUENCE: 16

```
catgcgttga ataatattaa actgtggacg aattcccaaa taagccacag ttatgcaaga      60
aacgctagaa aaataggta gtatttaata acgtgctgac taacatctgc ggataagagc     120
tttgcgtttt gaggtactaa ccacaata                                        148
```

<210> SEQ ID NO 17
<211> LENGTH: 148
<212> TYPE: RNA
<213> ORGANISM: Drosophila ananassae

<400> SEQUENCE: 17

```
uuaggcguuc aaaacauuaa acguuggcug auuuaugauu aggcuagugu uaugcacgca      60
acgcuagaga aaauugguag uauuuaauaa ugcguuggug gcaaaucuau cgauuuugau     120
```
cuucgcauuu ugagguacua gcacaguu                                                148

<210> SEQ ID NO 18
<211> LENGTH: 148
<212> TYPE: DNA
<213> ORGANISM: Drosophila ananassae

<400> SEQUENCE: 18
ttaggcgttc aaaacattaa acgttggctg atttatgatt aggctagtgt tatgcacgca    60
acgctagaga aaattggtag tatttaataa tgcgttggtg gcaaatctat cgattttgat   120
cttcgcattt tgaggtacta gcacagtt                                      148

<210> SEQ ID NO 19
<211> LENGTH: 145
<212> TYPE: RNA
<213> ORGANISM: Drosophila pseudoobscura

<400> SEQUENCE: 19
cauggcgcuc aaacauuaau cgguggccug auccacacgu cggccacauu uaugcacgca    60
gcgccagaua auaguaggca gcauuuaaua auguauuggu uccaaaugac ucagacuuuu   120
gcauuuugag guguuagcca caacg                                         145

<210> SEQ ID NO 20
<211> LENGTH: 145
<212> TYPE: DNA
<213> ORGANISM: Drosophila pseudoobscura

<400> SEQUENCE: 20
catggcgctc aaacattaat cgtggcctg atccacacgt cggccacatt tatgcacgca    60
gcgccagata atagtaggca gcatttaata atgtattggt tccaaatgac tcagactttt   120
gcattttgag gtgttagcca caacg                                         145

<210> SEQ ID NO 21
<211> LENGTH: 145
<212> TYPE: RNA
<213> ORGANISM: Drosophila persimilis

<400> SEQUENCE: 21
cauggcgcuc aaacauuaau cgguggccug auccacacgu cggccacauu uaugcacgca    60
gcgccagaua auaguaggca gcauuuaaua auguauuggu uccaaaugac ucagacuuuu   120
gcauuuugag guguuagcca caaag                                         145

<210> SEQ ID NO 22
<211> LENGTH: 145
<212> TYPE: DNA
<213> ORGANISM: Drosophila persimilis

<400> SEQUENCE: 22
catggcgctc aaacattaat cgtggcctg atccacacgt cggccacatt tatgcacgca    60
gcgccagata atagtaggca gcatttaata atgtattggt tccaaatgac tcagactttt   120
gcattttgag gtgttagcca caaag                                         145

<210> SEQ ID NO 23
<211> LENGTH: 149
<212> TYPE: RNA
<213> ORGANISM: Drosophila willistoni

<400> SEQUENCE: 23
agaggcguuc aacauuuaac uuuagccguu cuuuuaaacu aagcuauuug uuaugcaagu    60
aacgcuagaa uauaauuucu gcaacauuua auaaugcuuu ggucguauac uaacaaaaau   120
cucagcauuu ugaggugucu gcuacaauu                                    149

<210> SEQ ID NO 24
<211> LENGTH: 149
<212> TYPE: DNA
<213> ORGANISM: Drosophila willistoni

<400> SEQUENCE: 24
agaggcgttc aacatttaac tttagccgtt cttttaaact aagctatttg ttatgcaagt    60
aacgctagaa tataatttct gcaacattta ataatgcttt ggtcgtatac taacaaaaat   120
ctcagcattt tgaggtgtct gctacaatt                                    149

<210> SEQ ID NO 25
<211> LENGTH: 141
<212> TYPE: RNA
<213> ORGANISM: Drosophila mojavensis

<400> SEQUENCE: 25
cccugcguug agcaguaaau ugucgcugau ugauaauuag gcgacgauaa ugcaaacaac    60
gguagaaaaa acuaacgaca uuuaauaaua cauugaccac uaaaucccau gaacauugca   120
uuuugaggug ucgcgacaug u                                            141

<210> SEQ ID NO 26
<211> LENGTH: 141
<212> TYPE: DNA
<213> ORGANISM: Drosophila mojavensis

<400> SEQUENCE: 26
ccctgcgttg agcagtaaat tgtcgctgat tgataattag gcgacgataa tgcaaacaac    60
ggtagaaaaa actaacgaca tttaataata cattgaccac taaatcccat gaacattgca   120
ttttgaggtg tcgcgacatg t                                            141

<210> SEQ ID NO 27
<211> LENGTH: 142
<212> TYPE: RNA
<213> ORGANISM: Drosophila virilis

<400> SEQUENCE: 27
uuaugcguuc aacaguaaau ugucgccgau agauuacuag gcgacaguua ugcaaggcaa    60
cgcuagaaua agcagacgac auuuaauaau gcauuggccg acaaacucca cggccuuugc   120
guuuugaggu gucgccacau gu                                           142

<210> SEQ ID NO 28
<211> LENGTH: 142
<212> TYPE: DNA
<213> ORGANISM: Drosophila virilis

<400> SEQUENCE: 28
ttatgcgttc aacagtaaat tgtcgccgat agattactag gcgacagtta tgcaaggcaa    60
cgctagaata agcagacgac atttaataat gcattggccg acaaactcca cggcctttgc   120
gttttgaggt gtcgccacat gt                                           142

```
<210> SEQ ID NO 29
<211> LENGTH: 141
<212> TYPE: RNA
<213> ORGANISM: Drosophila grimshawi

<400> SEQUENCE: 29
uugugcguuc gacaguaaau uuucgaugac uguagauagg cgaaaauuau gcaaggcaac     60
gcuagaccaa uuagaugacg acauuuaaua augcauuggc cgauuaacuc agaucuugca    120
uuuugaggug ucgccacaug u                                              141

<210> SEQ ID NO 30
<211> LENGTH: 141
<212> TYPE: DNA
<213> ORGANISM: Drosophila grimshawi

<400> SEQUENCE: 30
ttgtgcgttc gacagtaaat tttcgatgac tgtagatagg cgaaaattat gcaaggcaac     60
gctagaccaa ttagatgacg acatttaata atgcattggc cgattaactc agatcttgca    120
ttttgaggtg tcgccacatg t                                              141

<210> SEQ ID NO 31
<211> LENGTH: 17
<212> TYPE: DNA
<213> ORGANISM: artificial sequence
<220> FEATURE:
<223> OTHER INFORMATION: target sequence within the gene Ir56d

<400> SEQUENCE: 31
tggttgaatt cacaaaa                                                    17

<210> SEQ ID NO 32
<211> LENGTH: 16
<212> TYPE: DNA
<213> ORGANISM: artificial sequence
<220> FEATURE:
<223> OTHER INFORMATION: target sequence within the gene buttonhead

<400> SEQUENCE: 32
ttgaattcac aaaata                                                     16

<210> SEQ ID NO 33
<211> LENGTH: 16
<212> TYPE: DNA
<213> ORGANISM: artificial sequence
<220> FEATURE:
<223> OTHER INFORMATION: target sequence within the gene klarsicht

<400> SEQUENCE: 33
aattcacaaa ataggc                                                     16

<210> SEQ ID NO 34
<211> LENGTH: 16
<212> TYPE: DNA
<213> ORGANISM: artificial sequence
<220> FEATURE:
<223> OTHER INFORMATION: target sequence within the gene CG3262

<400> SEQUENCE: 34
aagcgttaga tattaa                                                     16

<210> SEQ ID NO 35
<211> LENGTH: 16
<212> TYPE: DNA
```

```
<213> ORGANISM: artificial sequence
<220> FEATURE:
<223> OTHER INFORMATION: target sequence within the genes CG30502 and
      CG11125

<400> SEQUENCE: 35
acatctgcgg ataaga                                                      16

<210> SEQ ID NO 36
<211> LENGTH: 16
<212> TYPE: DNA
<213> ORGANISM: artificial sequence
<220> FEATURE:
<223> OTHER INFORMATION: target sequence within the gene CG9339

<400> SEQUENCE: 36
aagctttgcg ttttga                                                      16

<210> SEQ ID NO 37
<211> LENGTH: 16
<212> TYPE: DNA
<213> ORGANISM: artificial sequence
<220> FEATURE:
<223> OTHER INFORMATION: target sequence within the gene CG40006

<400> SEQUENCE: 37
agaagctttg cgtttt                                                      16

<210> SEQ ID NO 38
<211> LENGTH: 149
<212> TYPE: RNA
<213> ORGANISM: Drosophila melanogaster

<400> SEQUENCE: 38
aaaagcguua gauauuaaac uggguugaa uucacaaaau aggccacagu uaugcaauaa         60
acgcuagaaa aaaaacggua guauuuaaua acguuugac uaacaucugc ggauaagaag        120
cuuugcguuu ugagguacua accacagua                                        149

<210> SEQ ID NO 39
<211> LENGTH: 150
<212> TYPE: RNA
<213> ORGANISM: Drosophila simulans

<400> SEQUENCE: 39
gaaagcguua gguauaaacc ugugguugaa uucacaaaau aggccacagu uaugcaauaa        60
acgcuagaaa aaaaacggua guauuuaaua acguuugac uaacaucugc ggauaaaaca       120
gcuuugcguu uugagguacu aaccacagua                                       150

<210> SEQ ID NO 40
<211> LENGTH: 150
<212> TYPE: RNA
<213> ORGANISM: Drosophila sechellia

<400> SEQUENCE: 40
gaaagcguua gguauuaacc ugugguuuaa uucacaaaau aggccacagu uaugcaauaa        60
acgcuagaaa aaaaacggua guauuuaaua acguuugac uaacaucugc ggauaaaaua       120
gcuuugcguu uugagguacu aaccacagua                                       150

<210> SEQ ID NO 41
<211> LENGTH: 148
<212> TYPE: RNA
```

```
<213> ORGANISM: Drosophila yakuba

<400> SEQUENCE: 41
gcaagcguug uauaauauua aacuguggaa acuucacaaa uaggccacag uuaugcaaga        60
aacgcuagaa aaacuuggua guauuuaaua acgugcugac uaacgucugc ggauaaaagc       120
uuugcguuuu gagguacuaa ccacauua                                         148

<210> SEQ ID NO 42
<211> LENGTH: 149
<212> TYPE: RNA
<213> ORGANISM: Drosophila erecta

<400> SEQUENCE: 42
gcaugcguug aauaauauua aacuguggac gaauucccaa auaagccaca guuaugcaag        60
aaacgcuaga aaaaauaggu aguauuuaau aacgugcuga cuaacaucug cggauaagag       120
cuuugcguuu ugagguacua accacaaua                                        149

<210> SEQ ID NO 43
<211> LENGTH: 143
<212> TYPE: RNA
<213> ORGANISM: Artificial Sequence
<220> FEATURE:
<223> OTHER INFORMATION: Consensus sequence

<400> SEQUENCE: 43
gaaagcguuc aacauuaaac uguggcggau ucaaaaauac gccagaguua ugcaagcaac        60
gcuagaaaaa auaggcagca uuuaauaaug uguugacuaa caacuggaua agagcuuugc       120
auuuugaggu acuagccaca aua                                              143
```